United States Patent [19]
Schadt et al.

[11] Patent Number: 5,364,556
[45] Date of Patent: Nov. 15, 1994

[54] HALOVINYL-DERIVATIVES

[75] Inventors: Martin Schadt, Seltisberg, Switzerland; Frank Seils, Wieslet, Germany

[73] Assignee: Hoffmann-La Roche Inc., Nutley, N.J.

[21] Appl. No.: 50,477

[22] PCT Filed: Sep. 16, 1992

[86] PCT No.: PCT/EP92/02131
§ 371 Date: May 18, 1993
§ 102(e) Date: May 18, 1993

[87] PCT Pub. No.: WO98/07234
PCT Pub. Date: Apr. 15, 1993

[30] Foreign Application Priority Data

Sep. 30, 1991 [CH] Switzerland ............. 2887/91
Sep. 30, 1991 [CH] Switzerland ............. 2888/91
Apr. 8, 1992 [CH] Switzerland ............. 1139/92

[51] Int. Cl.$^5$ ............. C09K 19/52; C09K 19/34; C09K 19/30
[52] U.S. Cl. ............. 252/299.01; 252/299.61; 252/299.63; 252/299.64; 252/299.66
[58] Field of Search ............. 252/299.01, 299.61, 252/299.63, 299.64, 299.66; 544/3, 298, 335; 546/1; 549/369; 560/8, 128; 568/585

[56] References Cited

U.S. PATENT DOCUMENTS 4,267,388  5/1981  Drakes et al. ............. 568/642
5,013,476  5/1991  Boller et al. ............. 252/299.61
5,183,587  2/1993  Kitano et al. ............. 252/299.63

FOREIGN PATENT DOCUMENTS 268198  11/1987  European Pat. Off.
325796  12/1988  European Pat. Off.
330216   2/1989  European Pat. Off.
377469   5/1990  European Pat. Off.
4034508 10/1990  Germany.

OTHER PUBLICATIONS

Kitano, K., et al. Molecular Crystals and Liquid Crystals, vol. 191, pp. 205-209 (1990).
Derwent Abstract No. 91-141456/20.

*Primary Examiner*—Shean Wu
*Attorney, Agent, or Firm*—George M. Gould; George W. Johnston; John P. Parise

[57] ABSTRACT

$$R-\!\!\left\langle A^1\right\rangle\!\!-Z^1\!\!\left[\!\left\langle A^2\right\rangle\!\!-Z^2\right]_n\!\!\left[\!\left\langle A^3\right\rangle\!\!-Z^3\right]_p\!\!\left\langle A^4\right\rangle\!\!-Q-\!\!\underset{R^3}{\overset{R^2}{\diagup}}\!\!X^1 \quad (I)$$

Compounds of general formula (I), wherein R signifies hydrogen, halogen, cyano, isothiocyanato, or alkyl, alkenyl or alkynyl with 1 to 15 carbon atoms, which is unsubstituted or substituted with at least one of halogen, cyano and/or trifluoromethyl and in which one or more non-adjacent —CH$_2$— group(s) can be replaced by —O—, —S—, —CO—, —COO— and/or —OOC—; Q represents alkylene with 2 to 10 carbon atoms, which is unsubstituted or substituted with at least one fluorine and in which one —CH$_2$— group can be replaced by —O—, —S—, —COO—, or —OOC—, or —CH$_2$—, —CF$_2$—, —CHF— or a single covalent bond; A$^1$, A$^2$, A$^3$ each independently signify 1,4-phenylene, which is unsubstituted or substituted with at least one of halogen, cyano and/or methyl and in which, when it is unsubstituted, one or more —CH— groups can be replaced by nitrogen, or unsubstituted or cyano- or fluoro-substituted trans-1,4-cyclohexylene, or 1,4-cyclohexenylene, trans-1,3-dioxane-2,5-diyl or trans-1,3-dithiane-2,5-diyl; A$^4$ represents unsubstituted or cyano- or fluoro-substituted trans-1,4-cyclohexylene, or 1,4-cyclohexenylene, trans-1,3-dioxane-2,5-diyl, trans-1,3-dithiane-2,5-diyl or, when Q is different from a single covalent bond, also 1,4-phenylene, which is unsubstituted or substituted with at least one of halogen, cyano and/or methyl and in which, when it is unsubstituted, one or more —CH— groups can be replaced by nitrogen; X$^1$ represents bromine or chlorine; Z$^1$, Z$^2$, Z$^3$ each inde- (Abstract continued on next page.)

pendently denote a single covalent bond, $-CH_2O-$, $-OCH_2-$, $-CH_2CH_2-$, $-COO-$, $-OOC-$, $-C\equiv C-$, $-(CH_2)_4-$, $-(CH_2)_3O-$, $-O(CH_2)_3-$, the trans form of $-CH=CH-$, $-CH=CHCH_2O-$, $-OCH_2CH=CH-$, $-CH=CH(CH_2)_2-$ or $-(CH_2)_2CH=CH-$; n, p each independently signify 0 or 1; $R^2$, $R^3$ each independently represent hydrogen or fluorine, as well as liquid crystalline mixtures which contain such compounds and their use for electro-optical purposes.

17 Claims, No Drawings

HALOVINYL-DERIVATIVES

The present invention is concerned with liquid crystal components having a terminal halovinyl group, liquid crystalline mixtures which contain such compounds and the use of such compounds for electro-optical purposes.

Liquid crystals are used primarily as dielectrics in indicating devices, since the optical properties of such compounds can be influenced by an applied voltage. Electro-optical devices based on liquid crystals are well-known to a person skilled in the art and can be based on various effects. Such devices are, for example, cells having dynamic scattering, DAP cells (deformation of aligned phases), guest/host cells, TN cells having a "twisted nematic" structure, STN cells ("super-twisted nematic"), SBE cells ("super-birefringence effect") and OMI cells ("optical mode interference"). The most common indicating devices are based on the Schadt-Helfrich effect and have a twisted nematic structure.

The liquid crystal materials must have a good chemical and thermal stability and a good stability towards electric fields and electromagnetic radiation. Further, at the usual operating temperatures in as broad a range as possible they should have a suitable mesophase or in mixtures should bring about or support a mesophase (for example, a nematic or a cholesteric phase for the aforementioned cells), but nevertheless should have a sufficiently low viscosity-and in the cells should permit short response times, low threshold potentials and a high contrast. Further properties such as the electrical conductivity, the dielectric anisotropy and the optical anisotropy must fulfil different requirements depending on the field of application and type of cell.

Compounds which fulfil these requirements are provided by the present invention.

The invention is concerned with compounds of the general formula

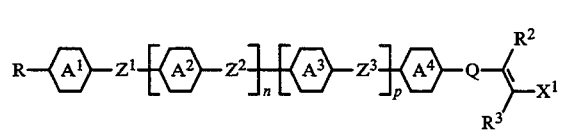

wherein

R signifies hydrogen, halogen, cyano, isothiocyanato, or alkyl, alkenyl or alkynyl with 1 to 15 carbon atoms, which is unsubstituted or substituted with at least one of halogen, cyano and/or trifluoromethyl and in which one or more non-adjacent —$CH_2$— groups can be replaced by —O—, —S—, —CO—, —COO— and/or —OOC—;

Q represents alkylene with 2 to 10 carbon atoms, which is unsubstituted or substituted with at least one fluorine and in which one —$CH_2$— group can be replaced by —O—, —S—, —COO— or —OOC—, or —$CH_2$—, —$CF_2$—, —CHF— or a single covalent bond;

$A^1, A^2, A^3$ each independently signify 1,4-phenylene, which is unsubstituted or substituted with at least one of halogen, cyano and/or methyl and in which, when it is unsubstituted, one or more —CH— groups can be replaced by nitrogen, or unsubstituted or cyano- or fluoro-substituted trans-1,4-cyclohexylene, or 1,4-cyclohexenylene, trans-1,3-dioxane-2,5-diyl or trans-1,3-dithiane-2,5-diyl;

$A^4$ represents unsubstituted or cyano- or fluoro-substituted trans-1,4-cyclohexylene, or 1,4-cyclohexenylene, trans-1,3-dioxane-2,5-diyl, trans-1,3-dithiane-2,5-diyl or, when Q is different from a single covalent bond, also 1,4-phenylene, which is unsubstituted or substituted with at least one of halogen, cyano and/or methyl and in which, when it is unsubstituted, one or more —CH— groups can be replaced by nitrogen;

$X^1$ represents bromine or chlorine;

$Z^1, Z^2, Z^3$ each independently denote a single covalent bond, —$CH_2O$—, —$OCH_2$—, —$CH_2CH_2$—, —COO—, —OOC—, —C≡C—, —$(CH_2)_4$—, —$(CH_2)_3O$—, —$O(CH_2)_3$—, the trans form of —CH=CH—, —CH=CHCH_2O—, —OCH_2CH=CH—, —CH=CH(CH_2)_2— or —$(CH_2)_2$CH=CH—;

n, p each independently signify 0 or 1;

$R^2, R^3$ each independently represent hydrogen or fluorine.

The compounds in accordance with the invention are characterized by the presence of a vinylic halogen atom. This gives a comparatively high positive contribution to the dielectric anisotropy. In particular, the ready polarizability of the halovinyl group contributes to a surprisingly favourable influencing of the mesophases and of the electro-optical properties of the compounds in accordance with the invention. Thus, the compounds in accordance with the invention exhibit e.g. high clearing points and low threshold potentials, but without having an undesirably high electrical conductivity.

In spite of the high clearing points, the compounds in accordance with the invention have a comparatively low viscosity and therefore have short switching times. The compounds are excellently suited for use, inter alia, in TN, STN cells and in actively addressed indicating devices.

Contrary to expectations, the halovinyl compounds in accordance with the invention have an extraordinary thermal stability and a good stability towards electromagnetic radiation and towards electric fields.

The outstanding properties of these compounds can be coordinated optimally to the desired applications by selecting the rings $A^1, A^2, A^3$ and $A^4$ as well as the residue R. Thus, for example, the elastic properties can be modified depending on the choice of R. Further, the optical anisotropy can be varied in a wide range; for example, the compounds of formula I in which rings $A^1, A^2$ and $A^3$ signify trans-1,4-cyclohexylene and/or trans-1,3-dioxane-2,5-diyl have low optical anisotropies and the compounds of formula I in which rings $A^1, A^2$ and $A^3$ signify unsubstituted or fluoro-substituted 1,4-phenylene have especially high optical anisotropies.

The term "alkyl, alkenyl or alkynyl with 1 to 15 carbon atoms, which is unsubstituted or substituted with at least one of halogen, cyano and/or trifluoromethyl and in which one or more non-adjacent —$CH_2$— groups can be replaced by —O—, —S—, —CO—, —COO— and/or —OOC—" embraces in the scope of the present invention straight-chain and branched (optionally chiral) residues with 1 to 15 carbon atoms such as alkyl, 1E-alkenyl, 3E-alkenyl, 4-alkenyl, alkenyl having a terminal double bond, alkoxy, 2E-alkenyloxy, 3-alkenyloxy, alkenyloxy having a terminal double bond, alkynyl, alkynyloxy, alkoxyalkynyl, alkoxyalkyl, alkenyloxyalkyl, alkoxyalkenyl, alkoxycarbonyl, alkoxycarbonylalkoxy, alkanoyloxy, 1-haloalkyl, 2-haloalkyl, 2-haloalkoxy, 2-halo- alkoxycarbonyl, 1-cyanoalkyl, 2-cyanoalkyl, 2-cyanoalkoxy, 2-cyanoalkoxycarbonyl, 1-methylalkyl, 2-methylalkyl, 1-methylalkoxy, 2-methylalkoxy, 2-methylalkoxycarbonyl and the like. Examples of preferred residues are methyl, ethyl, propyl, butyl, pentyl, hexyl, heptyl, octyl, nonyl, decyl, undecyl, dodecyl, 1-methylpropyl, 1-methylheptyl, 2-methylbutyl, 3-methylpentyl, vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4Z-heptenyl, 5-hexenyl, 6-heptenyl, 7-octenyl, 8-nonenyl, 9-decenyl, 10-undecenyl, 11-dodecenyl, methoxy, ethoxy, propyloxy, butyloxy, pentyloxy, hexyloxy, heptyloxy, octyloxy, nonyloxy, decyloxy, undecyloxy, dodecyloxy. 1-methylpropyloxy, 1-methylheptyloxy, 2-methylbutyloxy, 3-methylpentyloxy, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy, 7-octenyloxy, 8-nonenyloxy, 9-decenyloxy, 10-undecenyloxy, 11-dodecenyloxy, 3-methoxy-1E-propenyl, 3-ethoxy-1E-propenyl, 4-methoxy-1E-butenyl, 4-ethoxy-1E-butenyl, 2-propenyloxymethyl, 2Z-butenyloxymethyl, 3-butenyloxymethyl, ethynyl, 1-propynyl, 1-butynyl, 1-pentynyl, 3-butynyl, 3-pentynyl, 3-hexynyl, 2-propynyloxy, 2-butynyloxy, 2-pentynyloxy, 2-hexynyloxy, 3-methoxy-1-propynyl, 3-ethoxy-1-propynyl, methoxymethyl, ethoxymethyl, propyloxymethyl, allyloxymethyl, methoxyethyl, ethoxyethyl, propyloxyethyl, methoxypropyl, ethoxypropyl, propyloxypropyl, methoxybutyl, ethoxybutyl, propyloxybutyl, methoxycarbonyl, ethoxycarbonyl, propyloxycarbonyl, 1-methylpropyloxycarbonyl, 1-(methoxycarbonyl)ethoxy, 1-(ethoxycarbonyl)ethoxy, acetoxy, propionyloxy, butyryloxy, 1-fluoropropyl, 1-fluoropentyl, 1-chloropropyl, 2-fluoropropyl, 2-fluoropentyl, 2-chloropropyl, 2-fluoropropyloxy, 2-fluorobutyloxy, 2-fluoropentyloxy, 2-fluorohexyloxy, trifluoromethoxy, difluoromethoxy, 2-chloropropyloxy, 2-fluorobutyloxy, 2-fluoropropyl-oxycarbonyl, 2-fluorobutyloxycarbonyl, 2-fluoropentyloxycarbonyl, 2-fluoro-3-methylbutyloxycarbonyl, 2-fluoro-4-methylpentyloxycarbonyl, 2-chloropropyloxycarbonyl, 1-cyanopropyl, 1-cyanopentyl, 2-cyanopropyl, 2-cyanopentyl, 2-cyanopropyloxy, 2-cyanobutyloxy, 2-cyanopentyloxy, 2-cyanohexyloxy, 2-cyanopropyloxycarbonyl, 2-cyanobutyloxycarbonyl, 2-cyano-3-methylbutyloxycarbonyl, 2-cyano-4-methylpentyloxycarbonyl and the like. The aforementioned residues preferably have 1 to 9 carbon atoms, especially 1 to 7 carbon atoms.

The term "halogen" embraces in the scope of the present invention chlorine, fluorine, bromine and iodine, especially fluorine, chlorine and bromine.

The term "alkylene with 2 to 10 carbon atoms, which is unsubstituted or substituted with at least one fluorine and in which one —$CH_2$— group can be replaced by —O—, —S—, —COO— or —OOC—" embraces in the scope of the present invention alkylene residues with 2 to 10 carbon atoms such as, for example, ethylene, propylene, butylene, pentylene, hexylene, heptylene, octylene, nonylene, decylene; residues with 2 to 4 carbon atoms are especially preferred; alkyleneoxy residues with 2 to 10 chain atoms such as e.g. methyleneoxy, ethyleneoxy, propyleneoxy, butyleneoxy, pentyleneoxy, hexyleneoxy, heptyleneoxy, octyleneoxy, nonyleneoxy, especially residues with 2 to 4 chain atoms; alkyleneoxyalkyl residues with 3 to 10 chain atoms such as e.g. methyleneoxymethyl, ethyleneoxymethyl, propyleneoxymethyl, butyleneoxymethyl, pentyleneoxymethyl, hexyleneoxymethyl, heptyleneoxymethyl, octyleneoxymethyl and the like, especially with 3 to 4 chain atoms, alkylenoxycarbonyl residues such as, for example, methyleneoxycarbonyl, ethyleneoxycarbonyl, propyleneoxycarbonyl, butyleneoxycarbonyl, pentyleneoxycarbonyl, hexyleneoxycarbonyl, heptyleneoxycarbonyl, octyleneoxycarbonyl; and alkylenecarbonyloxy residues such as e.g. methylenecarbonyloxy, ethylenecarbonyloxy, propylenecarbonyloxy, butylenecarbonyloxy, pentylenecarbonyloxy, hexylenecarbonyloxy, heptylenecarbonyloxy, octylenecarbonyloxy and the like, whereby these residues can be optionally fluorinated. Such fluorinated residues are, for example, 1,2-difluoroethylene, perfluoroethylene, perfluoropropylene, perfluorobutylene and the like.

The term "unsubstituted or cyano- or fluoro-substituted trans-1,4-cyclohexylene" embraces in the scope of the present invention trans-1,4-cyclohexylene, 1-cyano-trans-1,4-cyclohexylene, 4-cyano-trans-1,4-cyclohexylene, 1-fluoro-trans-1,4-cyclohexylene, 4-fluoro-trans-1,4-cyclohexylene and the like, especially trans-1,4-cyclohexylene.

The term "1,4-phenylene, which is unsubstituted or substituted with at least one of halogen, cyano and/or methyl and in which, when it is unsubstituted, one or more —CH— groups can be replaced by nitrogen" embraces rings such as, for example, 1,4-phenylene, 2-fluoro-1,4-phenylene, 2,3-difluoro-1,4-phenylene, 2,6-difluoro-1,4-phenylene, 2,3,5,6-tetrafluoro-1,4-phenylene, 2-cyano-1,4-phenylene, 2,3-dicyano-1,4-phenylene, 2-chloro-1,4-phenylene, 2,3-dichloro-1,4-phenylene, 2,6-dichloro-1,4-phenylene, pyridine-2,5-diyl, pyrimidine-2,5-diyl, pyrazine-2,5-diyl and the like. 1,4-Phenylene, 2-fluoro-1,4-phenylene, 2,3-difluoro-1,4-phenylene and 2,6-difluoro-1,4-phenylene are especially preferred rings.

A preferred aspect of the invention is concerned with compounds of general formula I in which $A^1$, $A^2$, $A^3$ each independently represent 1,4-phenylene, which is unsubstituted or substituted with at least one of halogen and/or cyano, or pyridine-2,5-diyl, pyrimidine-2,5-diyl, trans-1,4-cyclohexylene or trans-1,3-dioxane-2,5-diyl; $A^4$ represents trans-1,4-cyclohexylene, trans-1,3-dioxane-2,5-diyl or, when Q is different from a single covalent bond, also 1,4-phenylene, which is unsubstituted or substituted with at least one of halogen, or pyridine-2,5-diyl or pyrimidine-2,5-diyl; $Z^1$, $Z^2$, $Z^3$ each independently represent a single covalent bond, —$CH_2O$—, —$OCH_2$—, —$CH_2CH_2$—, —COO—, —OOC— or —C≡C—; Q represents alkylene with 2 to 4 carbon atoms, which is unsubstituted or substituted with at least one of fluorine and in which one —$CH_2$— group can be replaced by —O—, —COO— or —OOC—, or —$CH_2$—, —$CF_2$—, —CHF— or a single covalent bond; R represents hydrogen, alkyl, alkenyl or alkynyl with 1 to 7 carbon atoms, which is unsubstituted or substituted with at least one of halogen, cyano and/or trifluoromethyl and in which one or more non-adjacent —$CH_2$— groups can be replaced by —O—, —COO— and/or —OOC—, or, where ring $A^1$ represents an aromatic ring, also halogen or cyano; $R^2$ and $R^3$ each independently represent hydrogen or fluorine, preferably hydrogen; and n, p and $X^1$ have the aforementioned significance.

In formula I, preferably a maximum of one of rings $A^1$, $A^2$, $A^3$ and $A^4$ stands for trans-1,3-dioxane-2,5-diyl, pyridine-2,5-diyl or pyrimidine-2,5-diyl.

Especially preferred compounds of the present invention are compounds of the general formula

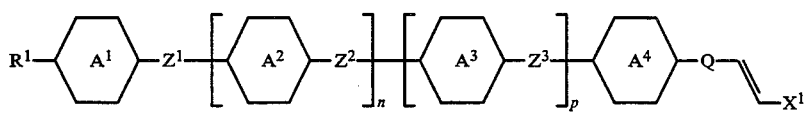

I-a wherein
$A^1$, $A^2$, $A^3$ each independently represent 1,4-phenylene, which is unsubstituted or substituted with at least one halogen, or pyridine-2,5-diyl, pyrimidine-2,5-diyl, trans-1,4-cyclohexylene or trans-1,3-dioxane-2,5-diyl;
$Z^1, Z^2, Z^3$ each independently signify a single covalent bond, —CH$_2$CH$_2$—, —OCH$_2$—, —CH$_2$O— or —C≡C—;
Q signifies —CH$_2$CH$_2$—, —OCH$_2$— or a single covalent bond;
$R^1$ signifies hydrogen, alkyl, alkenyl or alkynyl with 1 to 7 carbon atoms, which is unsubstituted or substituted with at least one of halogen, cyano and/or trifluoromethyl and in which one —CH$_2$— group can be replaced by —O—, or, where ring $A^1$ represents an aromatic ring, also halogen or cyano;
n, p each independently signify 0 or 1;
$A^4$ signifies trans-1,4-cyclohexylene, trans-1,3-dioxane-2,5-diyl or, when Q is different from a single covalent bond, also 1,4-phenylene, which is unsubstituted or substituted with at least one halogen, or pyridine-2,5-diyl or pyrimidine-2,5-diyl; and
$X^1$ represents chlorine or bromine.

Especially preferred compounds of formula I-a are compounds of the formula

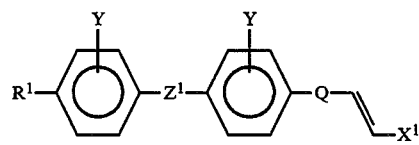
I-1

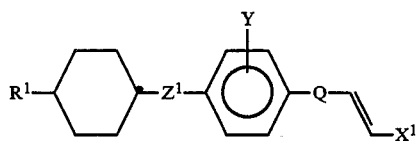
I-2

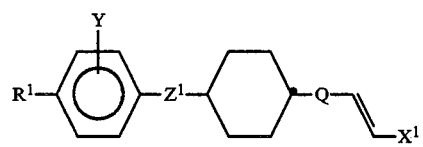
I-3

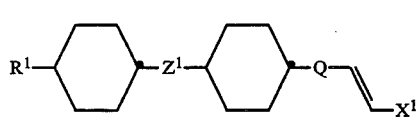
I-4

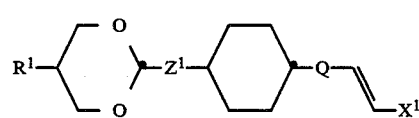
I-5

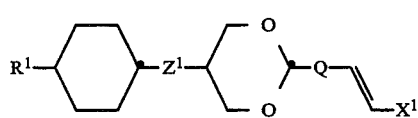
I-6

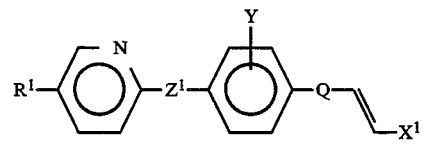
I-7

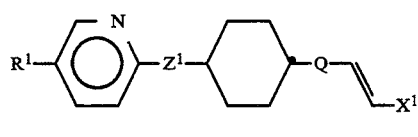
I-8

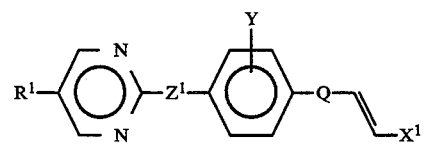
I-9

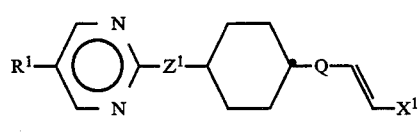
I-10

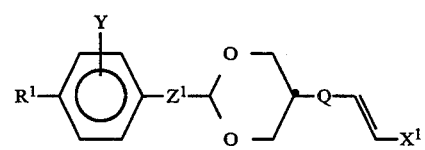
I-11

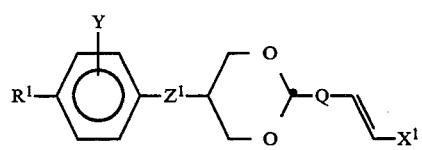
I-12

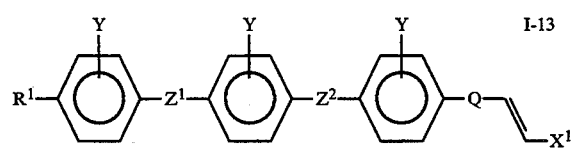
I-13

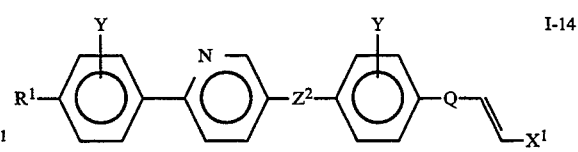
I-14

-continued
I-15 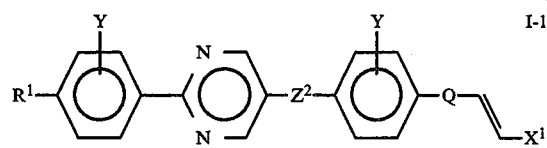
I-16 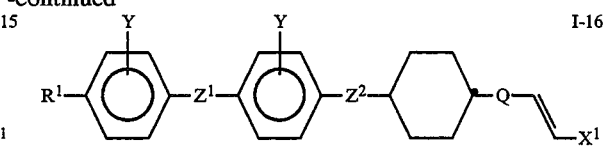
I-17 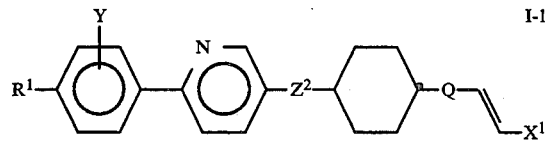
I-18 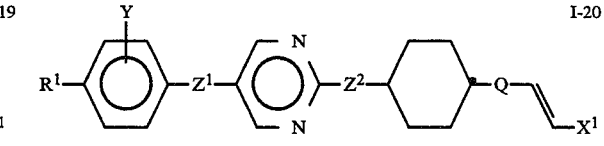
I-19 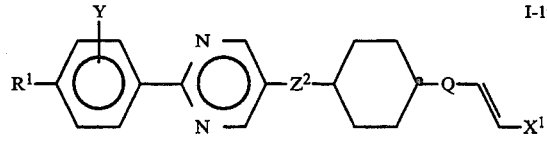
I-20 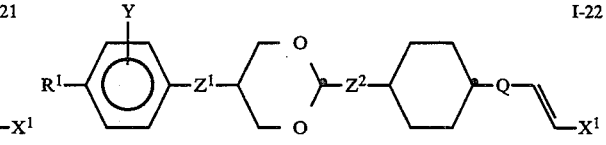
I-21 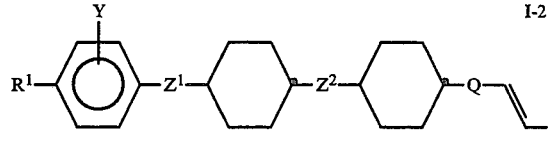
I-22 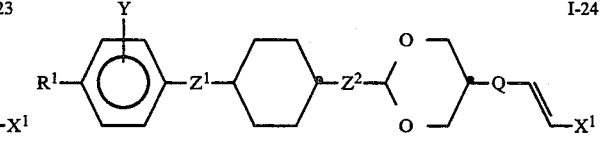
I-23 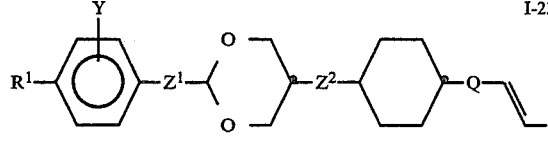
I-24 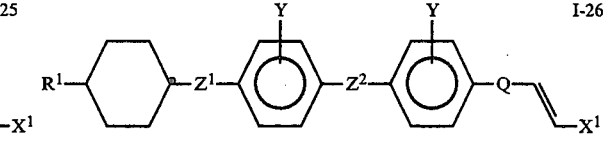
I-25 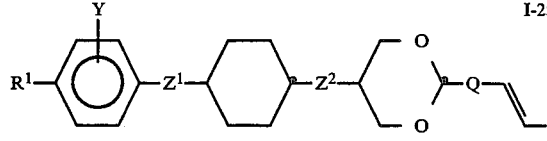
I-26 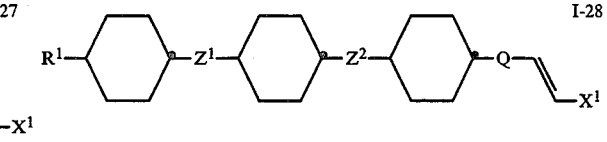
I-27 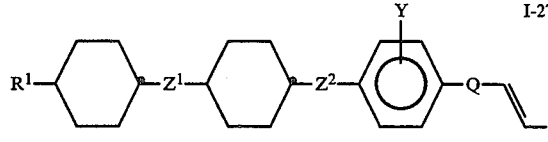
I-28 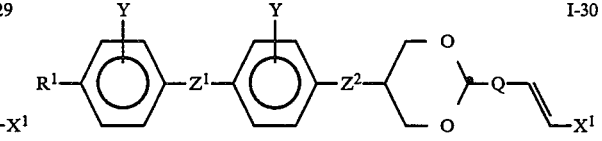
I-29 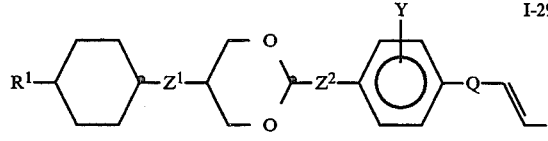
I-30 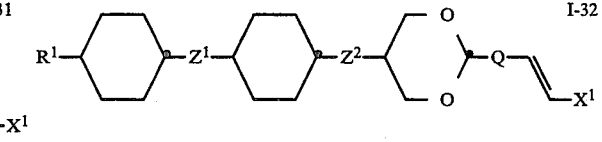
I-31 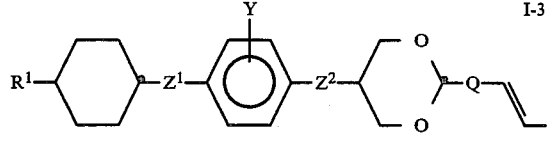
I-32 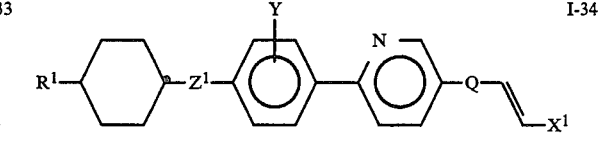
I-33 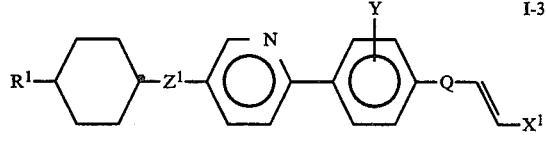
I-34 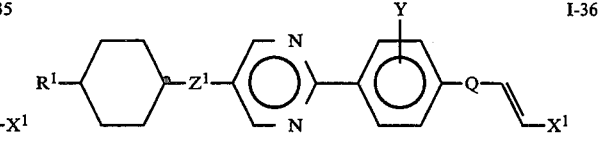
I-35 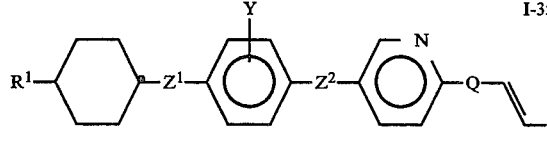

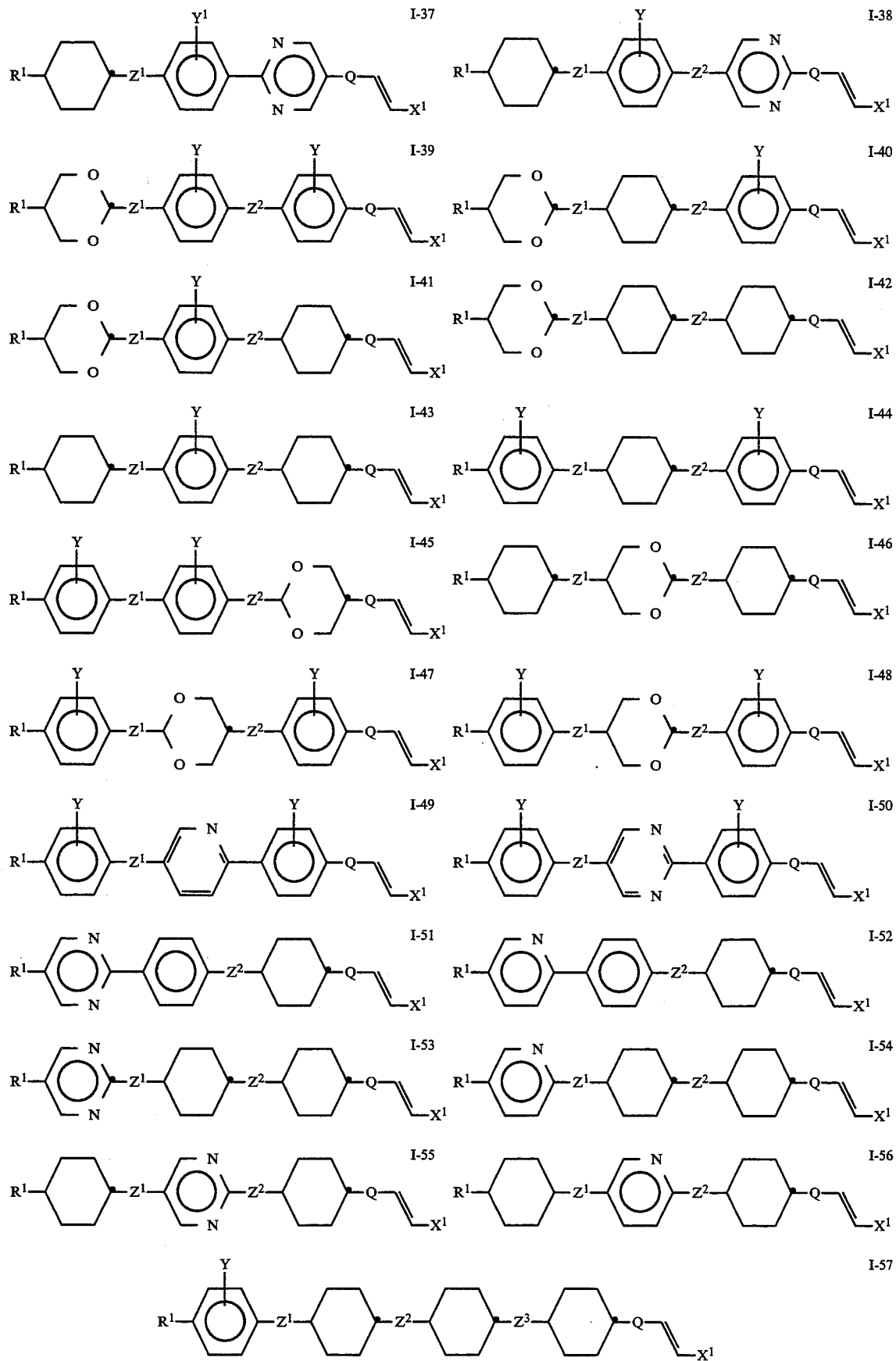

-continued
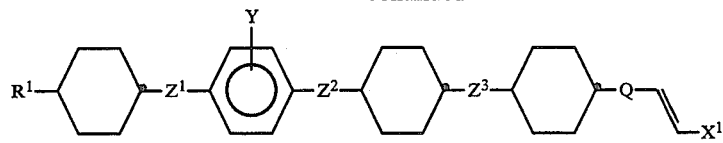
I-58
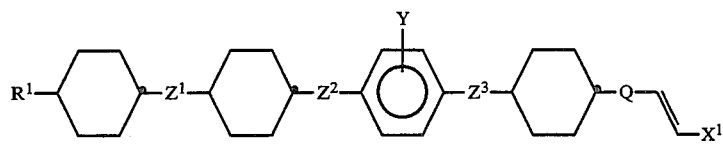
I-59
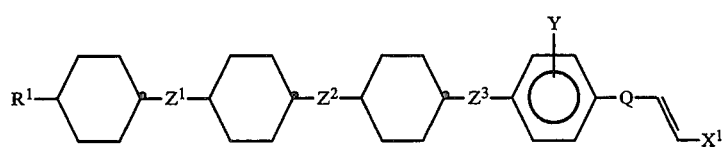
I-60
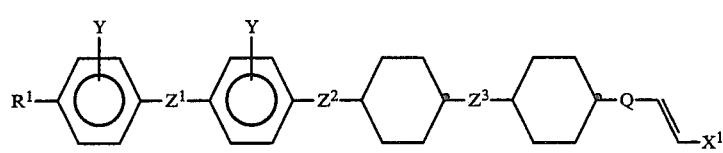
I-61
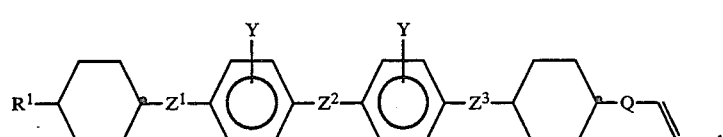
I-62
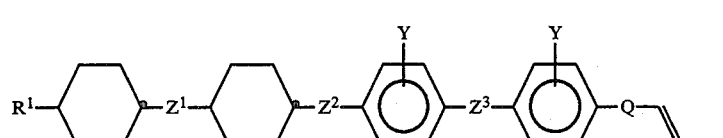
I-63
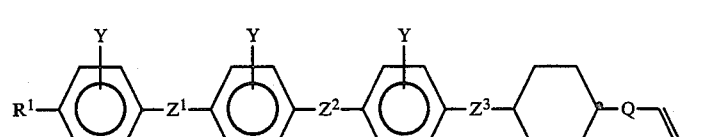
I-64
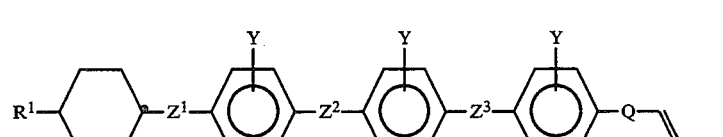
I-65
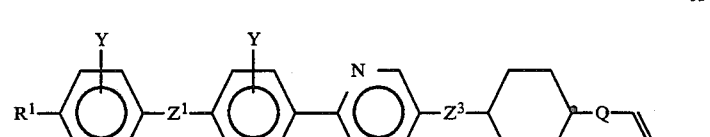
I-66
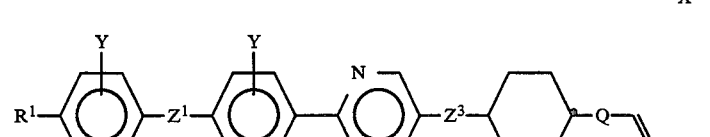
I-67
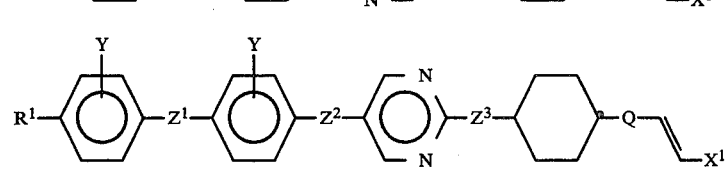
I-68

-continued
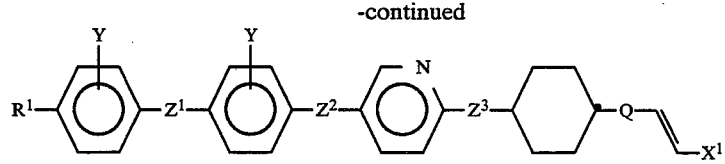
I-69
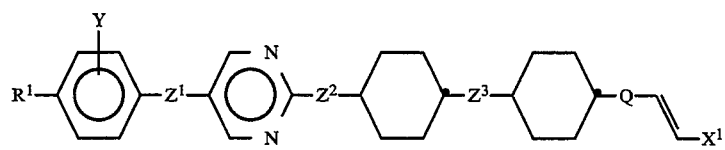
I-70
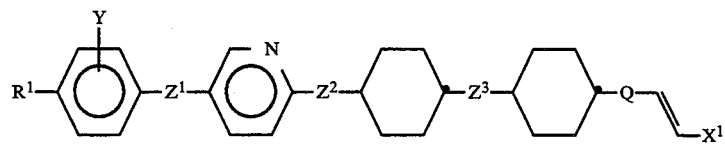
I-71
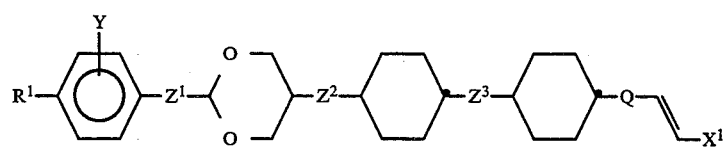
I-72
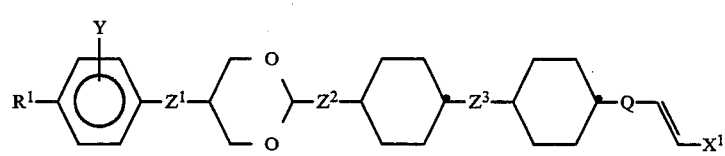
I-73
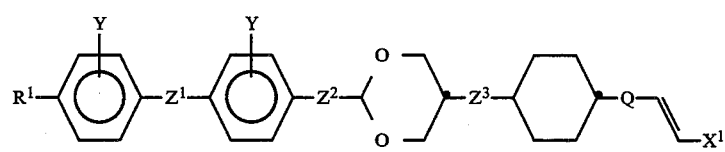
I-74
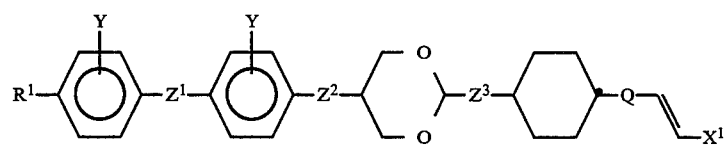
I-75
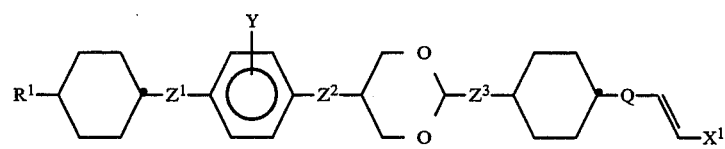
I-76
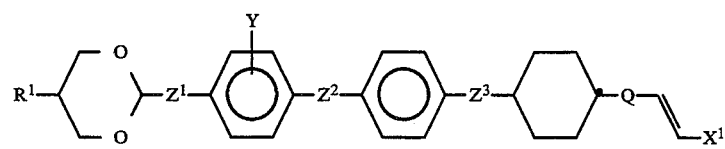
I-77
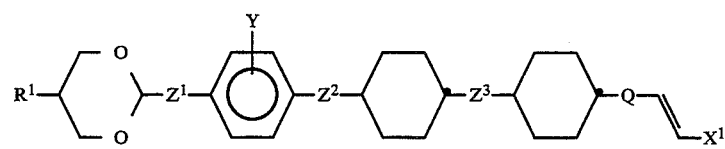
I-78
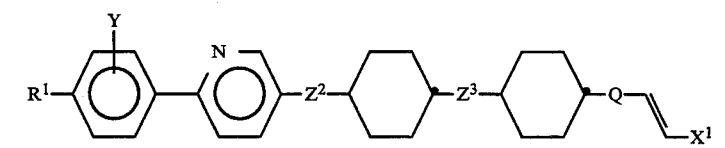
I-79

-continued

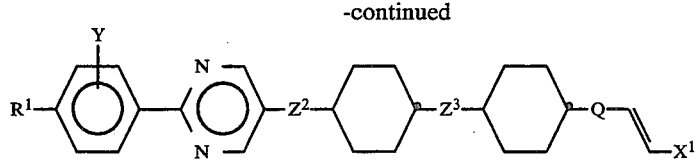 I-80

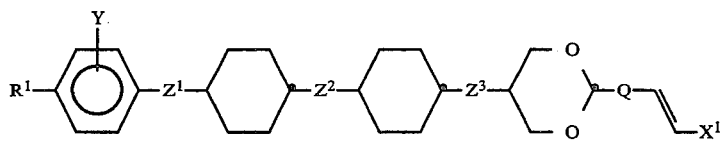 I-81

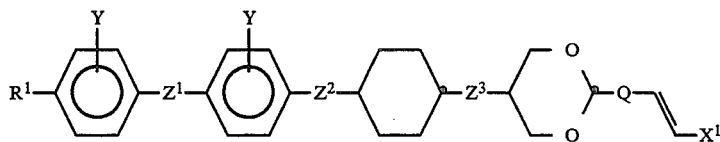 I-82

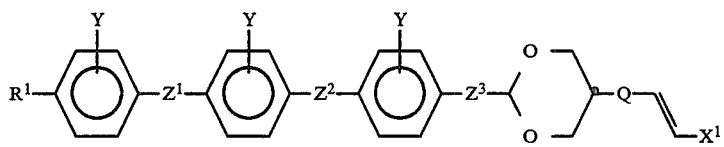 I-83

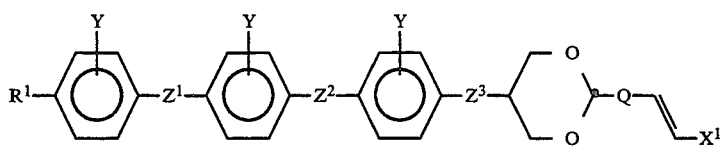 I-84 wherein $R^1$, $Z^1$, $Z^2$, $Z^3$, Q and $X^1$ have the significance given in formula I-a and the ring

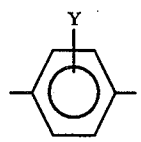

represents 1,4-phenylene, which is unsubstituted or substituted with at least one fluorine.

Especially preferred compounds of formula I-a are the compounds in which ring $A^4$ represents trans-1,4-cyclohexylene or, when Q is different from a single covalent bond, also 1,4-phenylene, which is unsubstituted or substituted with at least one fluorine.

Quite particularly preferred compounds of general formula

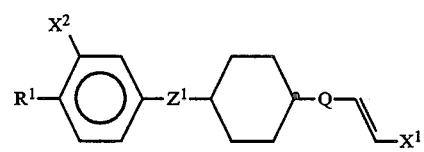 I-85

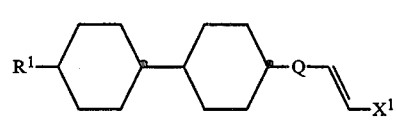 I-86

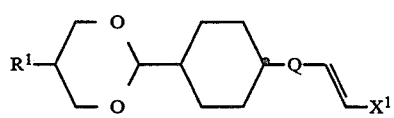 I-87

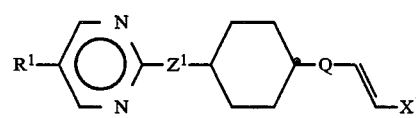 I-88

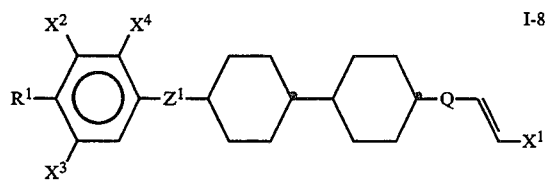 I-89

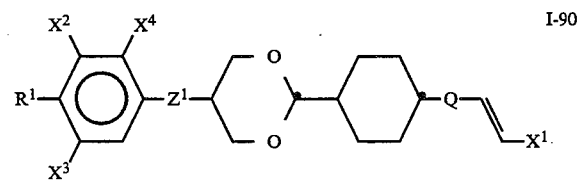 I-90

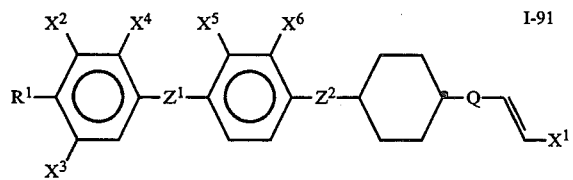 I-91

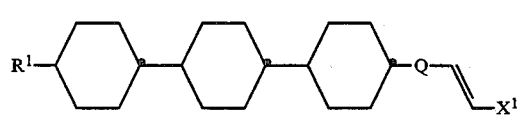 I-92

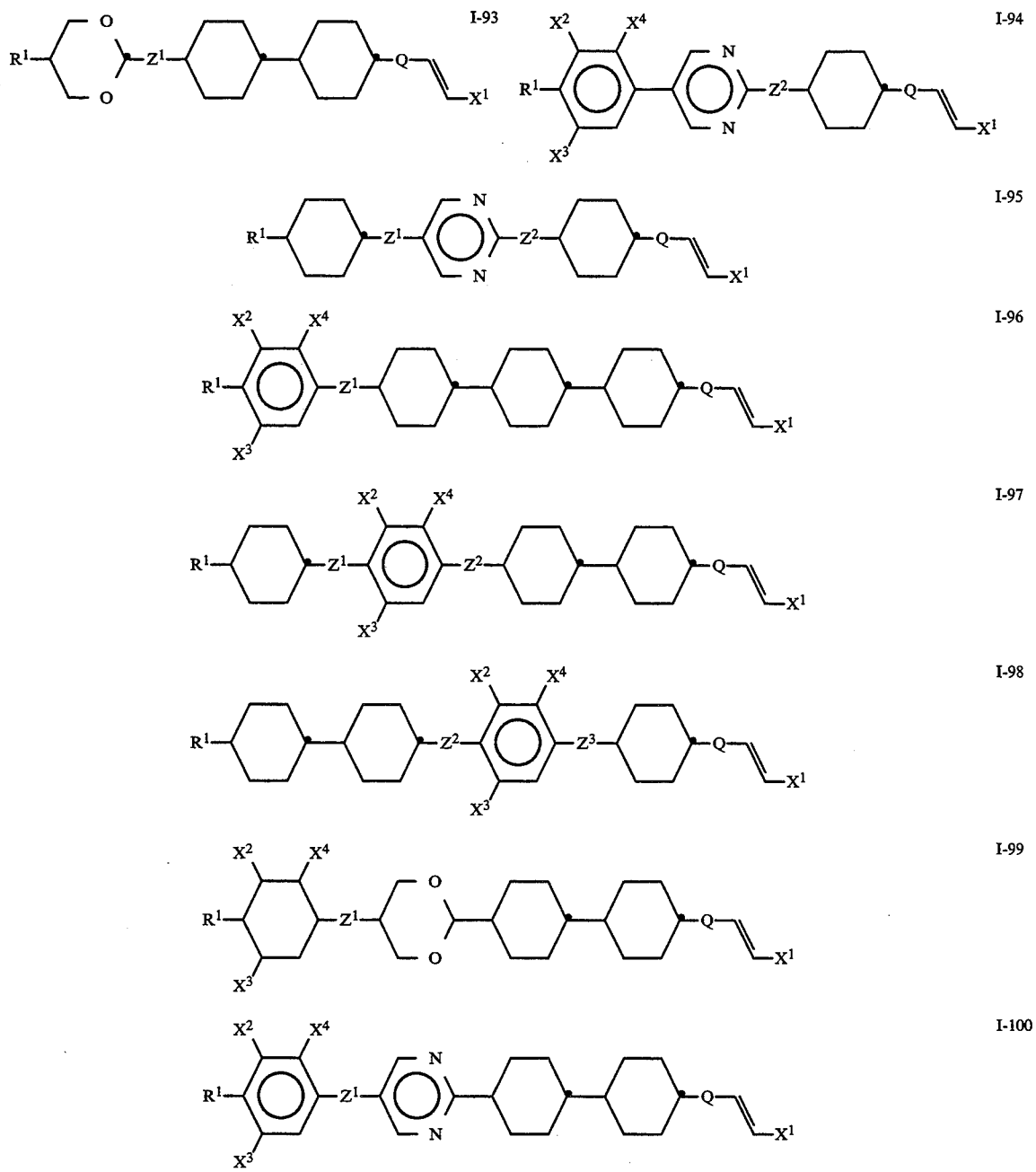

wherein
R¹ signifies hydrogen, alkyl, alkenyl or alkynyl with 1 to 5 carbon atoms, which is unsubstituted or substituted with at least one halogen and in which one —CH₂— group can be replaced by —O—, or on a phenyl ring also bromine, chlorine, fluorine or cyano;

$X^2, X^3, X^4, X^5, X^6$ each independently denote hydrogen or fluorine, with the proviso that $X^3$ and $X^4$ are not simultaneously fluorine;

$Z^1, Z^2, Z^3$ each independently signify a single covalent bond, —CH₂CH₂—, —CH₂O—, —OCH₂— or —C≡C—; preferably a maximum of one of groups $Z^1$, $Z^2$ and $Z^3$ stands for —CH₂CH₂—, —CH₂O—, —OCH₂— or —C≡C—.

Q has the significance given in formula I-a.
Of the compounds of general formulae I-85 to I-100 there are particularly preferred those compounds in which Q signifies a single covalent bond and $X^1$ signifies chlorine.

The compounds of general formula I in which $R^2$ and $R^3$ signify hydrogen can be manufactured in a manner known per se, e.g. by reacting a suitable aldehyde under Wittig conditions with a chloromethyl- or bromomethyltriphenylphosphonium halide, see Schemes 1 to 3.

Scheme 1

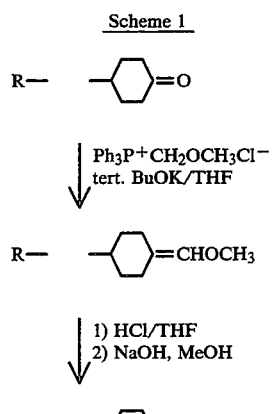

R— —⟨ ⟩— — =

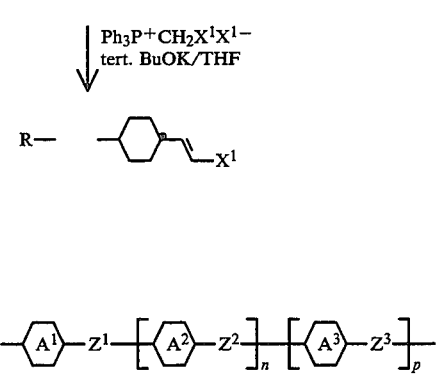

The double bond of the chloro- or bromovinyl sidechain produced in this manner usually occurs in an E/Z ratio of above 75% E-configuration and thus the pure E-isomer can be obtained by simple crystallization. Thereby, the isomerization of the double bond, which is to some extent costly, does not apply. The aldehydes which are used as starting materials are known and, where they are not commercially available, can be prepared in a manner known per se.

Scheme 2

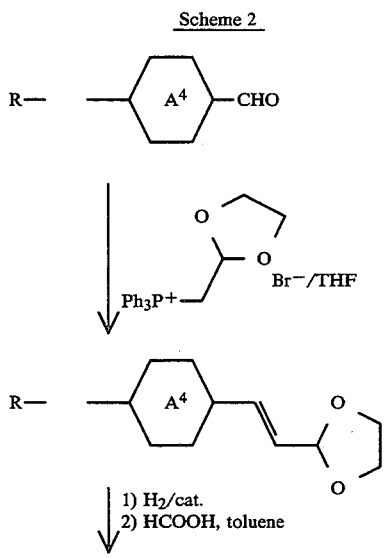

-continued
Scheme 2

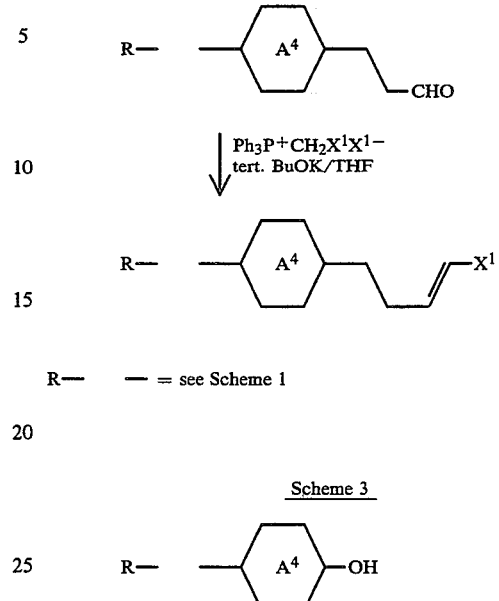

R— — = see Scheme 1

Scheme 3

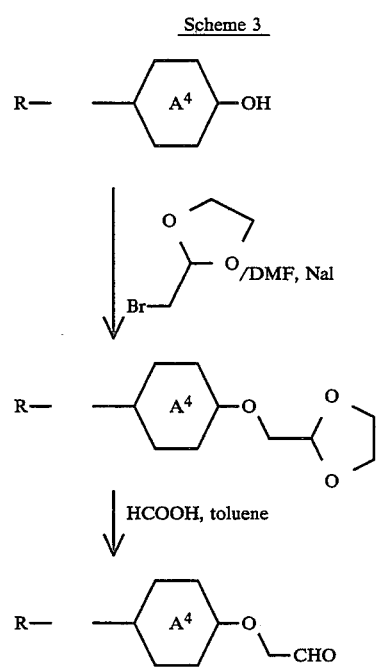

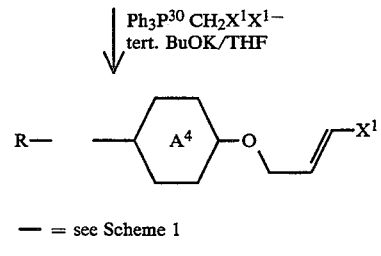

R— — = see Scheme 1

Because the steric hindrance of the ring system does not take place, the double bond produced in this manner occurs as a rule as an E/Z mixture in a ratio of about 1:1. It will be evident that the compounds can be used not only in the E-form or in the Z-form, but also as a mixture of isomers.

The compounds of formula I in which $R^2$ denotes hydrogen and $R^3$ signifies fluorine can also be manufactured from the aldehydes of the formula

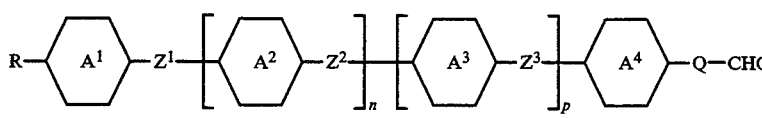 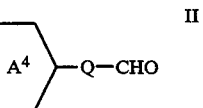

II wherein R, $A^1$, $A^2$, $A^3$, $A^4$, $Z^1$, $Z^2$, $Z^3$, Q, n and p have the above significance, under Wittig conditions with bromofluoromethyl- or chlorofluoromethyltriphenylphosphonium chloride [D. J. Burton, J. Fluorine Chem 23, (1983) 3391].

The compounds of formula I in which $R^2$ and $R^3$ signify fluorine can also be manufactured in a manner known per se, e.g. by the direct coupling of a suitable halide of the general formula

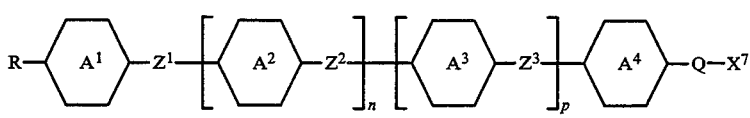 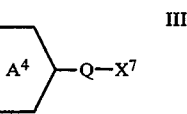

III wherein R, $A^1$, $A^2$, $A^3$, $A^4$, $Z^1$, $Z^2$, $Z^3$, Q, n and p have the above significance and $X^7$ signifies halogen, preferably iodine, with a suitable, prior-metallated difluoroethylene of the formula

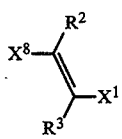

IV wherein $R^2$ and $R^3$ signify fluorine, $X^8$ represents chlorine, bromine or iodine; and $X^1$ denotes chlorine or bromine. Ethylenes of formula IV are known and their synthesis is described, for example, in CA 99/13-104740 and in J. Org. Chem. 30, 2121 (1965). The metallation of such ethylenes, for example with copper, is described in the literature (see e.g. J. March. "Advanced Organic Chemistry", McGraw-Hill, Tokio, 1977, p. 408f).

The compounds of formula I can be used in the form of mixtures with one another and/or with other liquid crystal components. Suitable liquid crystal components will be known in large numbers by a person skilled in the art. e.g. from D. Demus et al., Flüssige Kristalle in Tabellen, VEB Deutscher Verlag für Grundstoffindustrie, Leipzig, volumes I and II, and many of them are, moreover, commercially available.

The invention is therefore also concerned with a liquid crystalline mixture having at least two components, wherein at least one component is a compound formula I (especially a compound referred to as being preferred).

In mixtures, the compounds in accordance with the invention are distinguished by their chemical stability. Having regard to the good solubility on the one hand and on the other hand having regard to the wide range of variation of the properties and applications, the content of compounds of formula I in the mixtures in accordance with the invention can vary in a wide range. For example, the mixtures can consist exclusively of compounds of formula I. Alternatively, when R is chiral the compounds in accordance with the invention can also be used a chiral dopants. Such chiral dopants are frequently used only in relatively small amounts of e.g. about 0.1 to 10 wt. %. However, in general the content of compounds of formula I in the mixtures in accor- dance with the invention is about 1–60 wt. %. A range of as about 5–30 wt. % is generally preferred.

The mixtures in accordance with the invention for nematic or cholesteric applications preferably contain, in addition to one or more compounds of formula I, one more compounds from the group of compounds of the general formulae

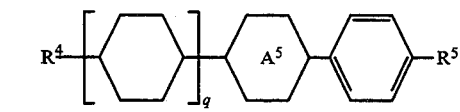

V

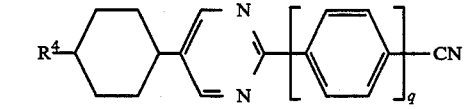

VI

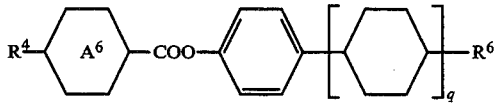

VII

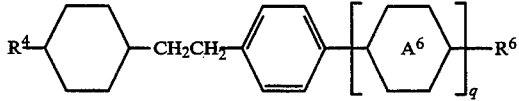

VIII

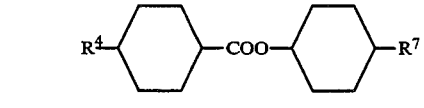

IX

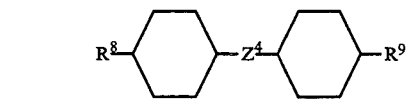

X

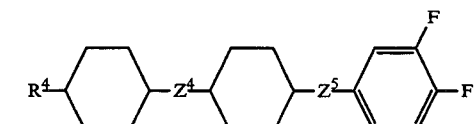

XI

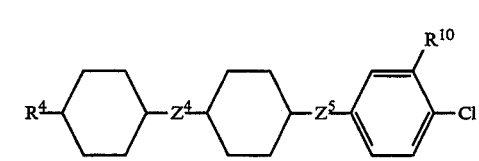

XII

-continued

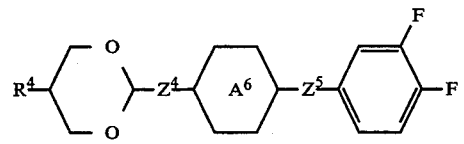 XIII

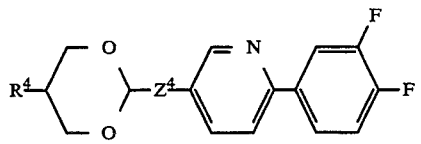 XIV

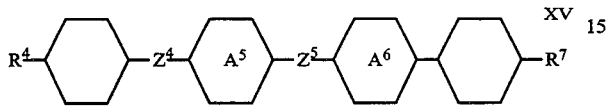 XV

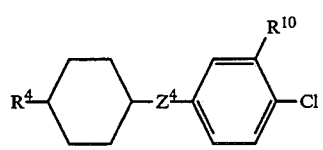 XVI

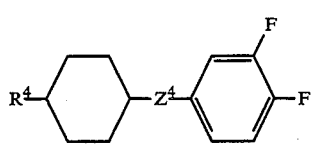 XVII

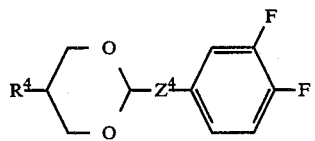 XVIII

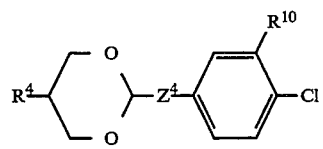 XIX

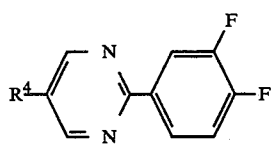 XX

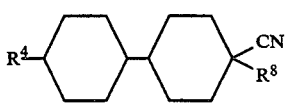 XXI

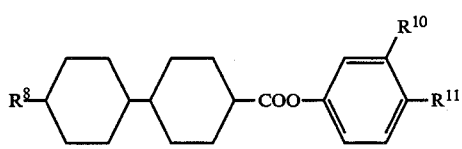 XXII

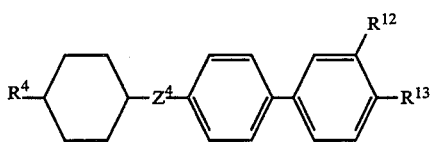 XXIII wherein $R^4$, $R^7$ signify alkyl, alkoxyalkyl, 3E-alkenyl, 4-alkenyl or on saturated rings also 1E-alkenyl;

q signifies 0 or 1;

ring $A^5$ denotes 1,4-phenylene, pyridine-2,5-diyl, pyrimidine-2,5-diyl, trans-1,4-cyclohexylene or trans-1,3-dioxane-2,5-diyl;

$R^5$ represents cyano, isothiocyanato, fluorine, alkyl, 3E-alkenyl, 4-alkenyl, alkoxy, 2E-alkenyloxy, 3-alkenyloxy or 1-alkynyl;

ring $A^6$ signifies 1,4-phenylene or trans-1,4-cyclohexylene;

$R^6$ denotes alkyl, 3E-alkenyl, 4-alkenyl or on trans-1,4-cyclohexylene also 1E-alkenyl or on 1,4-phenylene also cyano, isothiocyanato, alkoxy, 2E-alkenyloxy or 3-alkenyloxy;

$R^8$ signifies alkyl, 1E-alkenyl, 3E-alkenyl or 4-alkenyl;

$R^9$ represent cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl;

$Z^4, Z^5$ denote a single covalent bond or —CH$_2$CH$_2$—, with two aromatic rings always being linked by a single covalent bond;

$R^{10}$ signifies hydrogen, fluorine or chlorine;

$R^{11}$ represents cyano, fluorine or chlorine;

$R^{12}$ denotes hydrogen or fluorine; and $R^{13}$ represent fluorine or chlorine.

The term "aromatic ring" used above denotes in this connection rings such as 1,4-phenylene, pyridine-2,5-diyl and pyrimidine-2,5-diyl. The term "saturated ring" denotes trans-1,4-cyclohexylene and the trans-1,3-dioxane-2,5-diyl.

The residues $R^4$, $R^5$, $R^6$, $R^7$, $R^8$ and $R^9$ preferably have 1 to 12 carbon atoms, especially 1 to 7 carbon atoms.

The mixtures in accordance with the invention can also contain optically active compounds (e.g. optically active 4'-alkyl-or 4'-alkoxy-4-biphenylcarbonitriles) and/or dichroic colouring substances (e.g. azo, azoxy or anthraquinone colouring substances). The amount of such compounds is determined by the solubility, the desired helical pitch, colour, extinction and the like. In general, the amount of optically active compounds and dichroic colouring substances is in each case a maximum of about 10 wt. % in the finished mixture.

The manufacture of the liquid crystalline mixtures and of the electro-optical devices can be effected in a manner known per se.

The manufacture of the compounds of formula I and of liquid crystalline mixtures containing these compounds are illustrated in more detail by the following Examples. C signifies a crystalline phase, S signifies a smectic phase, N signifies a nematic phase and I signifies the isotropic phase. $V_{10}$ denotes the voltage for 10% transmission (viewing direction perpendicular to the plate surface). $t_{on}$ and $t_{off}$ denote the switching-on time and, respectively, the switching-off time and $\Delta n$ denotes the optical anisotropy.

EXAMPLE 1

1.2 g of chloromethyltriphenylphosphonium chloride were suspended in 10 ml of abs. tetrahydrofuran in a sulphonation flask while gassing with nitrogen and cooled to —20° C. 0.41 g of potassium tert.-butylate was added to this suspension, the suspension was stirred for 30 minutes and subsequently treated at —20° C. with a solution of 0.75 g of 4-chloro-4'-(4-trans-cyclohexylcarboxyaldehyde)-3-fluorobiphenyl in 5 ml of abs. tetrahydrofuran. The mixture was stirred at −20° C. for a further 40 minutes, poured into 50 ml of ice-cooled hexane and, after stirring at 0° C. for 90 minutes, filtered. From the filtrate there were isolated 1.06 g of crude 4-chloro-4'-{4-trans-[(E)-2-chlorovinyl]cyclohexyl}-3-fluorobiphenyl which was purified firstly by chromatography on silica gel with hexane and then by crystallization from methylene chloride/methanol. M.p. (C-N) 159.9° C., cl.p. (N-I) 204.5° C.

The following compounds can be manufactured in an analogous manner:

4-{4-trans-[(E)-2-chlorovinyl]cyclohexyl}-1-fluorobenzene 1-chloro-4-{4-trans-[(E)-2-chlorovinyl]cyclohexyl}benzene, m.p. (C-I) 117.2° C.
4-{4-trans-[(E)-2-chlorovinyl]cyclohexyl}-1-bromobenzene
4-{4-trans-[(E)-2-chlorovinyl]cyclohexyl}-1-methylbenzene
4-{4-trans-[(E)-2-chlorovinyl]cyclohexyl}-1-ethylbenzene
4-{4-trans-[(E)-2-chlorovinyl]cyclohexyl}-1-propylbenzene
4-{4-trans-[(E)-2-chlorovinyl]cyclohexyl}-1-butylbenzene
4-{4-trans-[(E)-2-chlorovinyl]cyclohexyl}-1-pentylbenzene
4-{4-trans-[(E)-2-chlorovinyl]cyclohexyl}-1-methoxybenzene
4-{4-trans-[(E)-2-chlorovinyl]cyclohexyl}-1-ethoxybenzene
4-{4-trans-[(E)-2-chlorovinyl]cyclohexyl}-1-propyloxybenzene
4-{4-trans-[(E)-2-chlorovinyl]cyclohexyl}-1-butyloxybenzene
4-{4-trans-[(E)-2-chlorovinyl]cyclohexyl}-1-pentyloxybenzene
4-{4-trans-[(E)-2-chlorovinyl]cyclohexyl}-1-methoxymethylbenzene
4-{4-trans-[(E)-2-chlorovinyl]cyclohexyl}-1-ethoxymethylbenzene
4-{4-trans-[(E)-2-chlorovinyl]cyclohexyl}-1-propyloxymethyl-benzene
4-{4-trans-[(E)-2-chlorovinyl]cyclohexyl}benzonitrile
4-{4-trans-[(E)-2-chlorovinyl]cyclohexyl}-1-(trifluoromethyl)benzene
4-{4-trans-[(E)-2-chlorovinyl]cyclohexyl}-1-(trifluoromethoxy)benzene, m.p. 47.2° C.
4-{4-trans-[(E)-2-chlorovinyl]cyclohexyl}-1-(difluoromethoxy)benzene
2-{4-trans-[(E)-2-chlorovinyl]cyclohexyl}-5-methylpyridine
2-{4-trans-[(E)-2-chlorovinyl]cyclohexyl}-5-ethylpyridine
2-{4-trans-[(E)-2-chlorovinyl]cyclohexyl}-5-propylpyridine
2-{4-trans-[(E)-2-chlorovinyl]cyclohexyl}-5-butylpyridine
2-{4-trans-[(E)-2-chlorovinyl]cyclohexyl}-5-pentylpyridine
2-{4-trans-[(E)-2-chlorovinyl]cyclohexyl}-5-methoxypyridine
2-{4-trans-[(E)-2-chlorovinyl]cyclohexyl}-5-ethoxypyridine
2-{4-trans-[(E)-2-chlorovinyl]cyclohexyl}-5-propyloxypyridine
2-{4-trans-[(E)-2-chlorovinyl]cyclohexyl}-5-methoxymethylpyridine
2-{4-trans-[(E)-2-chlorovinyl]cyclohexyl}-5-ethoxymethylpyridine
2-{4-trans-[(E)-2-chlorovinyl]cyclohexyl}-5-propyloxymethylpyridine
2-{4-trans-[(E)-2-chlorovinyl]cyclohexyl}-5-methylpyrimidine
2-{4-trans-[(E)-2-chlorovinyl]cyclohexyl}-5-ethylpyrimidine
2-{4-trans-[(E)-2-chlorovinyl]cyclohexyl}-5-propylpyrimidine
2-{4-trans-[(E)-2-chlorovinyl]cyclohexyl}-5-butylpyrimidine
2-{4-trans-[(E)-2-chlorovinyl]cyclohexyl}-5-pentylpyrimidine
2-{4-trans-[(E)-2-chlorovinyl]cyclohexyl}-5-methoxypyrimidine
2-{4-trans-[(E)-2-chlorovinyl]cyclohexyl}-5-ethoxypyrimidine
2-{4-trans-[(E)-2-chlorovinyl]cyclohexyl}-5-propyloxypyrimidine
2-{4-trans-[(E)-2-chlorovinyl]cyclohexyl}-5-methoxymethylpyrimidine
2-{4-trans-[(E)-2-chlorovinyl]cyclohexyl}-5-ethoxymethylpyrimidine
2-{4-trans-[(E)-2-chlorovinyl]cyclohexyl}-5-propyloxymethylpyrimidine
2-trans-{4-trans-[(E)-2-chlorovinyl]cyclohexyl}-5-methyl-m-dioxane
2-trans-{4-trans-[(E)-2-chlorovinyl]cyclohexyl}-5-ethyl-m-dioxane
2-trans-{4-trans-[(E)-2-chlorovinyl]cyclohexyl}-5-propyl-m-dioxane, m.p. (C-N) 46,8° C., d.p. (N-I) 56,0° C.
2-trans-{4-trans-[(E)-2-chlorovinyl]cyclohexyl}-5-butyl-m-dioxane
2-trans-{4-trans-[(E)-2-chlorovinyl]cyclohexyl}-5-pentyl-m-dioxane, m.p. (C-S) 17.9° C., S-N 26.3° C., cl.p. (N-I) 68.1° C.
2-trans-{4-trans-[(E)-2-chlorovinyl]cyclohexyl}-5-methoxy-m-dioxane
2-trans-{4-trans-[(E)-2-chlorovinyl]cyclohexyl}-5-ethoxy-m-dioxane
2-trans-{4-trans-[(E)-2-chlorovinyl]cyclohexyl}-5-propyloxy-m-dioxane
2-trans-{4-trans-[(E)-2-chlorovinyl]cyclohexyl}-5-butyloxy-m-dioxane
2-trans-{4-trans-[(E)-2-chlorovinyl]cyclohexyl}-5-pentyloxy-m-dioxane
2-trans-{4-trans-[(E)-2-chlorovinyl]cyclohexyl}-5-methoxymethyl-m-dioxane
2-trans-{4-trans-[(E)-2-chlorovinyl]cyclohexyl}-5-ethoxymethyl-m-dioxane
2-trans-{4-trans-[(E)-2-chlorovinyl]cyclohexyl}-5-propyloxymethyl-m-dioxane
2-trans-{4-trans-[(E)-2-chlorovinyl]cyclohexyl}-5-vinyl-m-dioxane
2-trans-{4-trans-[(E)-2-chlorovinyl]cyclohexyl}-5-(1E-propenyl)-m-dioxane
2-trans-{4-trans-[(E)-2-chlorovinyl]cyclohexyl}-5-(3-butenyl)-m-dioxane
2-trans-{4-trans-[(E)-2-chlorovinyl]cyclohexyl}-5-(3E-pentenyl)-m-dioxane
2-trans-{4-trans-[(E)-2-chlorovinyl]cyclohexyl}-5-(4-pentenyl)-m-dioxane
4'-trans-[(E)-2-chlorovinyl]-4-trans-ethynyl(1,1'-bicyclohexyl)
4'-trans-[(E)-2-chlorovinyl]-4-trans-methyl(1,1'-bicyclohexyl)

4'-trans-[(E)-2-chlorovinyl]-4-trans-ethyl(1,1'-bicyclohexyl)

4'-trans-[(E)-2-chlorovinyl]-4-trans-propyl(1,1'-bicyclohexyl), m.p. (C-N) 30.6° C., cl.p. (N-I) 101.6° C.

4'-trans-[(E)-2-chlorovinyl]-4-trans-butyl(1,1'-bicyclohexyl)

4'-trans-[(E)-2-chlorovinyl]-4-trans-pentyl(1,1'-bicyclohexyl)

4'-trans-[(E)-2-chlorovinyl]-4-trans-methoxy(1,1'-bicyclohexyl)

4'-trans-[(E)-2-chlorovinyl]-4-trans-ethoxy(1,1'-bicyclohexyl), m.p. (C-N) 57.8° C., cl.p. (N-I) 71.4° C.

4'-trans-[(E)-2-chlorovinyl]-4-trans-propyloxy(1,1'-bicyclohexyl)

4'-trans-[(E)-2-chlorovinyl]-4-trans-butyloxy(1,1'-bicyclohexyl)

4'-trans-[(E)-2-chlorovinyl]-4-trans-pentyloxy(1,1'-bicyclohexyl)

4'-trans-[(E)-2-chlorovinyl]-4-trans-methoxymethyl(1,1'-bicyclohexyl), m.p. (C-N) 38.1° C., cl.p. (N-I) 80.8° C.

4'-trans-[(E)-2-chlorovinyl]-4-trans-ethoxymethyl(1,1'-bicyclohexyl)

4'-trans-[(E)-2-chlorovinyl]-4-trans-propyloxymethyl(1,1'-bicyclohexyl)

4'-trans-[(E)-2-chlorovinyl]-4-trans-vinyl(1,1'-bicyclohexyl)

4'-trans-[(E)-2-chlorovinyl]-4-trans-(1E-propenyl)(1,1'-bicyclohexyl), m.p. (C-N) 74.1° C., cl.p. (N-I) 129.5° C.

4'-trans-[(E)-2-chlorovinyl]-4-trans-(3-butenyl)(1,1'-bicyclohexyl)

4'-trans-[(E)-2-chlorovinyl]-4-trans-(3E-pentenyl)(1,1'-bicyclohexyl)

4'-trans-[(E)-2-chlorovinyl]-4-trans-(4-pentenyl)(1,1'-bicyclohexyl)

1-(2-bromoethynyl)-4-{4-trans-[(E)-2-chlorovinyl]cyclohexyl}benzene 1-chloro-4-{2-[4-trans-[(E)-2-chlorovinyl]cyclohexyl]ethyl}benzene, m.p. (C-I) 67.0° C.

1-bromo-4-{2-[4-trans-[(E)-2-chlorovinyl]cyclohexyl]ethyl}benzene

4-{2-[4-trans-[(E)-2-chlorovinyl]cyclohexyl]ethyl}-1-fluorobenzene

4-{2-[4-trans-[(E)-2-chlorovinyl]cyclohexyl]ethyl}-1-bromobenzene

4-{[4-trans-[(E)-2-chlorovinyl]cyclohexyl]methoxy}benzonitrile 2-trans-{2-[4-trans-[(E)-2-chlorovinyl]cyclohexyl]ethyl}-5-propyl-m-dioxane 4-{4-trans-[(E)-2-chlorovinyl]cyclohexyl}-1,2-difluorobenzene 1-chloro-4-{4-trans-[(E)-2-chlorovinyl]cyclohexyl}-2-fluorobenzene, m.p. (C-I) 57.9° C.

1-bromo-4-{4-trans-[(E)-2-chlorovinyl]cyclohexyl}-2-fluorobenzene

4-{4-trans-[(E)-2-chlorovinyl]cyclohexyl}-2-fluorobenzonitrile

4-{4-trans-[(E)-2-chlorovinyl]cyclohexyl}-2-fluoro-1-(trifluoromethyl)benzene

4-{4-trans-[(E)-2-chlorovinyl]cyclohexyl}-2-fluoro-1-(trifluoromethoxy)benzene

4-{4-trans-[(E)-2-chlorovinyl]cyclohexyl}-2-fluoro-1-(difluoromethoxy)benzene

4-{4-trans-[(E)-2-chlorovinyl]cyclohexyl}-2-fluorotoluene

4-{2-[4-trans-[(E)-2-chlorovinyl]cyclohexyl]ethyl}-1-ethyl-2-fluorobenzene

4-{[4-trans-[(E)-2-chlorovinyl]cyclohexyl]methoxy}-2,3-difluoro-1-propylbenzene 2-chloro-4-{2-[4-trans-[(E)-2-chlorovinyl]cyclohexyl]ethyl}benzonitrile 4-{2-[4-trans-[(E)-2-chlorovinyl]cyclohexyl]ethyl}-1,2-difluorobenzene 1-chloro-4-{2-[4-trans-[(E)-2-chlorovinyl]cyclohexyl]ethyl}-2-fluorobenzene 1-bromo-4-{2-[4-trans-[(E)-2-chlorovinyl]cyclohexyl]ethyl}-2-fluorobenzene 4-{2-[4-trans-[(E)-2-chlorovinyl]cyclohexyl]ethyl}-2-fluorobenzonitrile 2-chloro-4-{4-[4-trans-[(E)-2-chlorovinyl]cyclohexyl]butyl}-1-(trifluoromethyl)benzene 4-{2-[4-trans-[(E)-2-chlorovinyl]cyclohexyl]ethyl}-2-fluoro-1-(trifluoromethoxy)benzene 4-{2-[4-trans-[(E)-2-chlorovinyl]cyclohexyl]ethyl}-2-fluoro-1-(difluoromethoxy)benzene 2-[4-trans-(2-chloroethyl)cyclohexyl]-1-{4-trans-[(E)-2-chlorovinyl]cyclohexyl}ethyne 4-{4'-trans-[(E)-2-chlorovinyl][1,1'-bicyclohexyl]-4-trans-yl}-1-fluorobenzene, m.p. (C-N) 103.3° C., cl.p. (N-I) 204.0° C.

1-chloro-4-{4'-trans-[(E)-2-chlorovinyl][1,1'-bicyclohexyl]-4-trans-yl}benzene, m.p. (C-S$_B$) 153° C., S$_B$-N 156° C.; cl.p. (N-I) 259° C.

1-bromo-4-{4'-trans-[(E)-2-chlorovinyl][1,1'-bicyclohexyl]-4-trans-yl}benzene, m.p. (C-N) 185.8° C., cl.p. (N-I) 265.2° C.

4-{4'-trans-[(E)-2-chlorovinyl][1,1'-bicyclohexyl]-4-trans-yl}-1-(trifluoromethyl)benzene 4-{4'-trans-[(E)-2-chlorovinyl][1,1'-bicyclohexyl]-4-trans-yl}-1-methoxy)benzene, m.p. (C-N) 87.7° C., cl.p. (N-I) 265.8° C.

1-ethoxy-4-{4'-trans-[(E)-2-chlorovinyl][1,1'-bicyclohexyl]-4-trans-yl}benzene, m.p. (C-N) 86.5° C., cl.p. (N-I) 267.5° C.

1-propyloxy-4-{4'-trans-[(E)-2-chlorovinyl][1,1'-bicyclohexyl]-4-trans-yl}benzene 1-methoxymethyl-4-{4'-trans-[(E)-2-chlorovinyl][1,1'-bicyclohexyl]-4-trans-yl}benzene 4-{4'-trans-[(E)-2-chlorovinyl][1,1'-bicyclohexyl]-4-trans-yl}-1-(trifluoromethoxybenzene, S$_B$-N 100.2° C., cl.p. (N-I) 200.6° C.

4-{4'-trans-[(E)-2-chlorovinyl][1,1'-bicyclohexyl]-4-trans-yl}-1-(difluoromethoxy)benzene, m.p. (C-S$_B$) 71.4° C., S$_B$-N 85.6° C., cl.p. (N-I) 223.5° C.

4-{4'-trans-[(E)-2-chlorovinyl][1,1'-bicyclohexyl]-4-trans-yl}benzonitrile, m.p. (C-N) 126.0° C., cl.p. (N-I) 307.8° C.

4-{4'-trans-[(E)-2-chlorovinyl][1,1'-bicyclohexyl]-4-trans-yl}toluene, m.p. (S-N) 99.6° C., cl.p. (N-I) 242.2° C.

1-ethyl-4-{4'-trans-[(E)-2-chlorovinyl][1,1'-bicyclohexyl]-4-trans-yl}benzene 1-propyl-4-{4'-trans-[(E)-2-chlorovinyl][1,1'-bicyclohexyl]-4-trans-yl}benzene 2-{4-[4-trans-[(E)-2-chlorovinyl]cyclohexyl]phenyl}-5-ethoxypyrimidine 1-{4-trans-[(E)-2-chlorovinyl]cyclohexyl}-4-(4-trans-propylcyclohexyl)benzene S-N 138.3° C., cl.p. (N-I) 214.7° C.

2-{4-[[4-trans-[(E)-2-chlorovinyl]cyclohexyl]oxymethyl]phenyl}-5-pentoxypyridine 2-trans-{4-[4-trans-[(E)-2-chlorovinyl]cyclohexyl]phenethyl}-5-butyl-m-dioxane 4-{4'-trans-[(E)-2-chlorovinyl][1,1'-bicyclohexyl]-4-trans-yl}-1,2-difluorobenzene, m.p. (C-N) 65.4° C., cl.p. (N-I) 173.7° C.

1-chloro-4-{4'-trans-[(E)-2-chlorovinyl][1,1'-bicyclohexyl]-4-trans-yl}-2-fluorobenzene, m.p. (C-N) 132.9° C., cl.p. (N-I) 226.3° C.

1-bromo-4-{4'-trans-[(E)-2-chlorovinyl][1.1'-bicyclohexyl]-4trans-yl}-2-fluorobenzene 4-{4'-trans-[(E)-2-chlorovinyl][1,1'-bicyclohexyl]-4-trans-yl}-2-fluorobenzonitrile 4-{4'-trans-[(E)-2-chlorovinyl][1,1'-bicyclohexyl]-4-trans-yl}-2-fluoro-1-(difluoromethoxy)benzene 4-{4'-trans-[(E)-2-chlorovinyl][1,1'-bicyclohexyl]-4-trans-yl}-2-fluoro-1-(trifluoromethoxy)benzene 1-{4'-trans-[(E)-2-chlorovinyl][1,1'-bicyclohexyl]-4-trans-yl}-3,5-difluorobenzene, m.p. (C-N) 90.8° C., cl.p. (N-I) 141.2° C.

{4'-trans-[(E)-2-chlorovinyl][1,1'-bicyclohexyl]-4-trans-yl}-1,2,6-trifluorobenzene 4-{4'-trans-[(E)-2-chlorovinyl][1,1'-bicyclohexyl]-4-trans-yl}-1-chloro-2,6-difluorobenzene 4-{4'-trans-[(E)-2-chlorovinyl][1,1'-bicyclohexyl]-4-trans-yl}-1-bromo-2,6-difluorobenzene 4-{4'-trans-[(E)-2-chlorovinyl][1,1'-bicyclohexyl]-4-trans-yl}-1-trifluoromethyl-2,6-difluorobenzene 4-{4'-trans-[(E)-2-chlorovinyl][1,1'-bicyclohexyl]-4-trans-yl}-1-trifluoromethoxy-2,6-difluorobenzene 4-{4'-trans-[(E)-2-chlorovinyl][1,1'-bicyclohexyl]-4-trans-yl}-1-difluoromethoxy-2,6-difluorobenzene 4-{4'-trans-[(E)-2-chlorovinyl][1,1'-bicyclohexyl]-4-trans-yl}-2,6-difluorobenzonitrile 4-{4'-trans-[(E)-2-chlorovinyl][1,1'-bicyclohexyl]-4-trans-yl}-2,6-difluorotoluene 4-{4'-trans-[(E)-2-chlorovinyl][1,1'-bicyclohexyl]-4-trans-yl}-1-ethyl-2,6-difluorobenzene 4-{4'-trans-[(E)-2-chlorovinyl][1,1'-bicyclohexyl]-4-trans-yl}-1-propyl-2,6-difluorobenzene 4-{4'-trans-[(E)-2-chlorovinyl][1,1'-bicyclohexyl]-4-trans-yl}-1-methoxy-2,6-difluorobenzene 4-{4'-trans-[(E)-2-chlorovinyl][1,1'-bicyclohexyl]-4-trans-yl}-1-ethoxy-2,6-difluorobenzene 4-{4'-trans-[(E)-2-chlorovinyl][1,1'-bicyclohexyl]-4-trans-yl}-1-propyloxy-2,6-difluorobenzene 4-{4'-trans-[(E)-2-chlorovinyl][1,1'-bicyclohexyl]-4-trans-yl}-1-methoxymethyl-2,6-difluorobenzene 4'-{2-[4-trans-[(E)-2-chlorovinyl]cyclohexyl]ethyl}-(3,2'-difluoro-4-trifluoromethoxy)biphenyl 5-trans-{4-trans-[(E)-2-chlorovinyl]cyclohexyl}-2-{[3-fluoro-4-(difluoromethoxy)]phenyl}-m-dioxane 5-{2-[4-trans-[(E)-2-chlorovinyl]cyclohexyl]ethyl}-2-{[3-fluoro-4-(trifluoromethyl)]phenyl}pyrimidine 4-{4'-trans-[(E)-2-chlorovinyl][1,1'-bicyclohexyl]-4-trans-yl}-2-fluorotoluene, m.p. (C-N) 100.3° C., cl.p. (N-I) 212.9° C.

1-ethyl-2-fluoro-4-{4'-trans-[(E)-2-chlorovinyl][1,1'-bicyclohexyl]-4-trans-yl}benzene 1-propyl-2-fluoro-4-{4'-trans-[(E)-2-chlorovinyl][1,1'-bicyclohexyl]-4-trans-yl}benzene 1-trifluoromethyl-2-fluoro-4-{4'-trans-[(E)-2chlorovinyl][1,1'-bicyclohexyl]-4-trans-yl}benzene 1-methoxy-2-fluoro-4-{4'-trans-[(E)-2-chlorovinyl][1,1'-bicyclohexyl]-4-trans-yl}benzene 1-ethoxy-2-fluoro-4-{4'-trans-[(E)-2-chlorovinyl][1,1'-bicyclohexyl]-4-trans-yl}benzene 1-propyloxy-2-fluoro-4-{4'-trans-[(E)-2-chlorovinyl][1,1'-bicyclohexyl]-4-trans-yl}benzene 1-methoxymethyl-2-fluoro-4-{4'-trans-[(E)-2-chlorovinyl][1,1'-bicyclohexyl]-4-trans-yl}benzene 4-trans-{4-[2-chloro-1,1,2,2-tetrafluoroethyl]phenyl}-4'-trans-[(E)-2-chlorovinyl](1,1'-bicyclohexyl)

4'-{2-[4-trans-[(E)-2-chlorovinyl]cyclohexyl]ethyl}-2,3-dicyano-4-propylbiphenyl 5-trans-(4-butylphenyl)-2-{4-trans-[(E)-2-chlorovinyl]cyclohexyl }-m-dioxane 4'-{4-trans-[(E)-2-chlorovinyl]cyclohexyl}-4-fluorobiphenyl 4-chloro-4'-{4-trans-[(E)-2-chlorovinyl]cyclohexyl}biphenyl, m.p. (C-N) 211.0° C., cl.p. (N-I) 266.5° C.

4-bromo-4'-{4-trans-[(E)-2-chlorovinyl]cyclohexyl}biphenyl 4-cyano-4'-{4-trans-[(E)-2-chlorovinyl]cyclohexyl}biphenyl 4-trifluoromethyl-4'-{4-trans-[(E)-2-chlorovinyl]cyclohexyl}biphenyl 4-trifluoromethoxy-4'-{4-trans-[(E)-2-chlorovinyl]cyclohexyl}biphenyl 4-difluoromethoxy-4'-{4-trans-[(E) -2-chlorovinyl]cyclohexyl}biphenyl 4-methyl-4'-{4-trans-[(E)-2-chlorovinyl]cyclohexyl}biphenyl 4-ethyl-4'-{4-trans-[(E)-2-chlorovinyl]cyclohexyl}biphenyl 4-propyl-4'-{4-trans-[(E)-2-chlorovinyl]cyclohexyl}biphenyl 4-methoxy-4'-{4-trans-[(E)-2-chlorovinyl]cyclohexyl}biphenyl 4-ethoxy-4'-{4-trans-[(E)-2-chlorovinyl]cyclohexyl}biphenyl 4-propyloxy-4'-{4-trans-[(E)-2-chlorovinyl]cyclohexyl}biphenyl 4-methoxymethyl-4'-{4-trans-[(E)-2-chlorovinyl]cyclohexyl}biphenyl 4'-{4-trans-[(E)-2-chlorovinyl]cyclohexyl}-3,4-difluorobiphenyl 4'-{4-trans-[(E)-2-chlorovinyl]cyclohexyl}-3-fluoro-4-chlorobiphenyl 4'-{4-trans-[(E)-2-chlorovinyl]cyclohexyl}-3-fluoro-4-bromobiphenyl 4'-{4-trans-[(E)-2-chlorovinyl]cyclohexyl}-3-fluoro-4-cyanobiphenyl 4'-{4-trans-[(E)-2-chlorovinyl]cyclohexyl}-3-fluoro-4-methylbiphenyl 4'-{4-trans-[(E)-2-chlorovinyl]cyclohexyl}-3-fluoro-4-ethylbiphenyl 4'-{4-trans-[(E)-2-chlorovinyl]cyclohexyl}-3-fluoro-4-propylbiphenyl 4'-{4-trans-[(E)-2-chlorovinyl]cyclohexyl}-3-fluoro-4-methoxybiphenyl 4'-{4-trans-[(E)-2-chlorovinyl]cyclohexyl}-3-fluoro-4-ethoxybiphenyl 4'-{4-trans-[(E)-2-chlorovinyl]cyclohexyl}-3-fluoro-4-propyloxybiphenyl 4'-{4-trans-[(E)-2-chlorovinyl]cyclohexyl}-3-fluoro-4-methoxymethylbiphenyl 4'-{4-trans-[(E)-2-chlorovinyl]cyclohexyl}-3-fluoro-4-trifluoromethylbiphenyl 4'-{4-trans-[(E)-2-chlorovinyl]cyclohexyl}-3-fluoro-4-trifluoromethoxybiphenyl 4'-{4-trans-[(E)-2-chlorovinyl]cyclohexyl}-3-fluoro-4-difluoromethoxybiphenyl 4'-{2-[4-trans-[(E)-2-chlorovinyl]cyclohexyl]ethyl}-4-(methoxymethyl)biphenyl 4'-{2-[4-trans-[(E)-2-chlorovinyl]cyclohexyl]ethyl}-4-fluorobiphenyl 4'-{2-[4-trans-[(E)-2-chlorovinyl]cyclohexyl]ethyl}-4-chlorobiphenyl 4'-{2-[4-trans-[(E)-2-chlorovinyl]cyclohexyl]ethyl}-4-bromobiphenyl 4'-{2-[4-trans-[(E)-2-chlorovinyl]cyclohexyl]ethyl}-4-cyanobiphenyl 4'-{2-[4-trans-[(E)-2-chlorovinyl]cyclohexyl]ethyl}-4-methylbiphenyl 4'-{2-[4-trans-[(E)-2-chlorovinyl]cyclohexyl]ethyl}-4-ethylbiphenyl 4'-{2-[4-trans-[(E)-2-chlorovinyl]cyclohexyl]ethyl}-4-propylbiphenyl 4'-{2-[4-trans-[(E)-2-chlorovinyl]cyclohexyl]ethyl}-4-methoxybiphenyl 4'-{2-[4-trans-[(E)-2-chlorovinyl]cyclohexyl]ethyl}-4-ethoxybiphenyl 4'-{2-[4-trans-[(E)-2-chlorovinyl]cyclohexyl]ethyl}-4-propyloxybiphenyl 4'-{2-[4-trans-[(E)-2-chlorovinyl]cyclohexyl]ethyl}-4-trifluoromethylbiphenyl 4'-{2-[4-trans-[(E)-2-chlorovinyl]cyclohexyl]ethyl}-4-trifluoromethoxybiphenyl 4'-{2-[4-trans-[(E)-2-chlorovinyl]cyclohexyl]ethyl}-4-difluoromethoxybiphenyl 4-(2-chloroethyl)-4'-{4-trans-[(E)-2-chlorovinyl]cyclohexyl}-2,3-difluorobiphenyl 4-trans-[(E)-2-chlorovinyl]-4'-trans-(4-fluorophenethyl)(1,1'-bicyclohexyl), m.p. (C-I) 103.3° C., cl.p. (N-I) 204.0° C.

4'-trans-(4-chlorophenethyl)-4-trans-[(E)-2-chlorovinyl](1,1'-bicyclohexyl)

4'trans-(4-bromophenethyl)-4-trans-[(E)-2-chlorovinyl](1,1'-bicyclohexyl), $S_B$-N 134.0° C., cl.p. (N-I) 207.5° C.

4'-trans-(4-trifluoromethylphenethyl)-4-trans-[(E)-2-chlorovinyl](1,1'-bicyclohexyl)

4'-trans-(4-trifluoromethoxyphenethyl)-4-trans-[(E)-2-chlorovinyl](1,1'-bicyclohexyl)

4'-trans-(4-difluoromethoxyphenethyl)-4-trans-[(E)-2-chlorovinyl](1,1'-bicyclohexyl)

4'-trans-(4-cyanophenethyl)-4-trans-[(E)-2-chlorovinyl](1,1'-bicyclohexyl)

4'-trans-(4-methylphenethyl)-4-trans-[(E)-2-chlorovinyl](1,1'-bicyclohexyl)

4'-trans-(4-ethylphenethyl)-4-trans-[(E)-2-chlorovinyl](1,1'-bicyclohexyl)

4'-trans-(4-propylphenethyl)-4-trans-[(E)-2-chlorovinyl](1,1'-bicyclohexyl)

4'-trans-(4-methoxyphenethyl)-4-trans-[(E)-2-chlorovinyl](1,1'-bicyclohexyl)

4'-trans-(4-ethoxyphenethyl)-4-trans-[(E)-2-chlorovinyl](1,1'-bicyclohexyl)

4'-trans-(4-propyloxyphenethyl)-4-trans-[(E)-2-chlorovinyl](1,1'-bicyclohexyl)

4'-trans-(4-methoxymethylphenethyl)-4-trans-[(E)-2-chlorovinyl](1,1'-bicyclohexyl)

4-trans-[(E)-2-chlorovinyl]-4'-trans-(3,4-difluorophenethyl)(1,1'-bicyclohexyl)

4'-trans-(4-chloro-3-fluorophenethyl)-4-trans-[(E)-2-chlorovinyl](1,1'-bicyclohexyl), m.p. (C-N) 95.5° C., cl.p. (N-I) 180.1° C.

4'-trans-(4-bromo-3-fluorophenethyl)-4-trans-[(E)-2-chlorovinyl](1,1'-bicyclohexyl)

4'-trans-(4-trifluoromethyl-3-fluorophenethyl)-4-trans-[(E)-2-chlorovinyl](1,1'-bicyclohexyl)

4'-trans-(4-trifluoromethoxy-3-fluorophenethyl)-4-trans-[(E)-2-chlorovinyl](1,1'-bicyclohexyl)

4'-trans-(4-difluoromethoxy-3-fluorophenethyl)-4-trans-[(E)-2-chlorovinyl](1,1'-bicyclohexyl)

4'-trans-(4-cyano-3-fluorophenethyl)-4-trans-[(E)-2-chlorovinyl](1,1'-bicyclohexyl)

4'-trans-(4-methyl-3-fluorophenethyl)-4-trans-[(E)-2-chlorovinyl](1,1'-bicyclohexyl)

4'-trans-(4-ethyl-3-fluorophenethyl)-4-trans-[(E)-2-chlorovinyl](1,1'-bicyclohexyl)

4'-trans-(4-propyl-3-fluorophenethyl)-4-trans-[(E)-2-chlorovinyl](1,1'-bicyclohexyl)

4'-trans-(4-methoxy-3-fluorophenethyl)-4-trans-[(E)-2-chlorovinyl](1,1'-bicyclohexyl)

4'-trans-(4-ethoxy-3-fluorophenethyl)-4-trans-[(E)-2-chlorovinyl](1,1'-bicyclohexyl)

4'-trans-(4-propyloxy-3-fluorophenethyl)-4-trans-[(E)-2-chlorovinyl](1,1'-bicyclohexyl)

4'-trans-(4-methoxymethyl-3-fluorophenethyl)-4-trans-[(E)-2-chlorovinyl](1,1'-bicyclohexyl)

4-trans-[(E)-2-chlorovinyl]-4'-trans-{[3,5-difluoro-4-(perfluoropropyl)phenoxy]methyl}(1,1'-bicyclohexyl)

1-(2-chloro-1,1,2,2-tetrafluoroethyl)-4-{4'-trans-[(E)-2-chlorovinyl][1,1'-bicyclohexyl]-4-trans-yl}benzene 4-{4'-trans-[(E)-2-chlorovinyl][1,1'-bicyclohexyl]-4-trans-yl}-1-(3,3,3-trifluoropropynyl)benzene 1,4-bis-{4-trans-[(E)-2-chlorovinyl]cyclohexyl}benzene 5-{2-[4-trans-[(E)-2-chlorovinyl]cyclohexyl]ethyl}-2-(3,4-difluorophenyl)pyrimidine 5-{2-[4-trans-[(E)-2-chlorovinyl]cyclohexyl]ethyl}-2-(4-chloro-3-fluorophenyl)pyridine 4-{4'-trans-[(E)-2-chlorovinyl][1,1'-bicyclohexyl]-4-trans-yl}phenylpropanoate 3,4-difluorophenyl 4'-trans-[(E)-2-chlorovinyl](1,1'-bicyclohexyl)-4-trans-carboxylate 4-trans-[(E)-2-chlorovinyl]-4'-trans-(3,5-difluorophenethyl)(1,1'-bicyclohexyl)

4-trans-[(E)-2-chlorovinyl]-4'-trans-(3,4,5-trifluorophenethyl)(1,1'-bicyclohexyl)

4-trans-[(E)-2-chlorovinyl]-4'-trans-(4-chloro-3,5-difluorophenethyl)(1,1'-bicyclohexyl)

4-trans-[(E)-2-chlorovinyl]-4'-trans-(4-bromo-3,5-difluorophenethyl)(1,1'-bicyclohexyl)

4'-trans-(4-trifluoromethyl-3,5-difluorophenethyl)-4-trans-[(E)-2-chlorovinyl](1,1'-bicyclohexyl)

4'-trans-(4-trifluoromethoxy-3.5-difluorophenethyl)-4-trans-[(E)-2-chlorovinyl](1,1'-bicyclohexyl)

4'-trans-(4-difluoromethoxy-3,5-difluorophenethyl)-4-trans-[(E)-2-chlorovinyl](1,1'-bicyclohexyl)

4'-trans-(4-cyano-3,5-difluorophenethyl)-4-trans-[(E)-2-chlorovinyl](1,1'-bicyclohexyl)

4'-trans-(4-methyl-3,5-difluorophenethyl)-4-trans-[(E)-2-chlorovinyl](1,1'-bicyclohexyl)

4'-trans-(4-ethyl-3,5-difluorophenethyl)-4-trans-[(E)-2-chlorovinyl](1,1'-bicyclohexyl)

4'-trans-(4-propyl-3,5-difluorophenethyl)-4-trans-[(E)-2-chlorovinyl](1,1'-bicyclohexyl)

4'-trans-(4-methoxy-3,5-difluorophenethyl)-4-trans-[(E)-2-chlorovinyl](1,1'-bicyclohexyl)

4'-trans -(4-ethoxy-3,5-difluorophenethyl)-4-trans-[(E)-2-chlorovinyl](1,1'-bicyclohexyl)

4'-trans-(4-propyloxy-3,5-difluorophenethyl)-4-trans-[(E)-2-chlorovinyl](1,1'-bicyclohexyl)

4'-trans-(4-methoxymethyl-3,5-difluorophenethyl)-4-trans-[(E)-2-chlorovinyl](1,1'-bicyclohexyl)

4'-trans-(4-trifluoromethyl-2,3-difluorophenethyl)-4-trans-[(E)-2-chlorovinyl](1,1'-bicyclohexyl)

4'-trans-(4-trifluoromethoxy -2,3-difluorophenethyl)-4-trans-[(E)-2-chlorovinyl](1,1'-bicyclohexyl)

4'-trans-(4-difluoromethoxy-2,3-difluorophenethyl)-4-trans-[(E)-2-chlorovinyl](1,1'-bicyclohexyl)

4'-trans-(4-cyano-2,3-difluorophenethyl)-4-trans-[(E)-2-chlorovinyl](1,1'-bicyclohexyl)
4'-trans-(2,3,4-trifluorophenethyl)-4-trans-[(E)-2-chlorovinyl](1,1'-bicyclohexyl)
4'-trans-(4-chloro-2,3-difluorophenethyl)-4-trans-[(E)-2-chlorovinyl](1,1'-bicyclohexyl)
4'-trans-(4-bromo-2,3-difluorophenethyl)-4-trans-[(E)-2-chlorovinyl](1,1'-bicyclohexyl)
4'-trans-(4-methyl-2,3-difluorophenethyl)-4-trans-[(E)-2-chlorovinyl](1,1'-bicyclohexyl)
4'-trans-(4-ethyl-2,3-difluorophenethyl)-4-trans-[(E)-2-chlorovinyl](1,1'-bicyclohexyl)
4'-trans-(4-propyl-2,3-difluorophenethyl)-4-trans-[(E)-2-chlorovinyl](1,1'-bicyclohexyl)
4'-trans-(4-methoxy-2,3-difluorophenethyl)-4-trans-[(E)-2-chlorovinyl](1,1'-bicyclohexyl)
4'-trans-(4-ethoxy-2,3-difluorophenethyl)-4-trans-[(E)-2-chlorovinyl](1,1'-bicyclohexyl)
4'-trans-(4-propyloxy-2,3-difluorophenethyl)-4-trans-[(E)-2-chlorovinyl](1,1'-bicyclohexyl)
4'-trans-(4-methoxymethyl-2,3-difluorophenethyl)-4-trans-[(E)-2-chlorovinyl](1,1'-bicyclohexyl)
1-{4'-trans-[(E)-2-chlorovinyl][1,1'-bicyclohexyl]-4-trans-yl}-4-(4-trans-propylcyclohexyl)benzene, S-N 231° C., cl.p. (N-I) 385° C.
4,4'-bis-{4-trans-[(E)-2-chlorovinyl]cyclohexyl}biphenyl
4'-trans-[(E)-2-chlorovinyl]-4"-trans-(4-fluorophenyl)(trans-1,1':4',1"-tercyclohexane)
4'-trans-[(E)-2-chlorovinyl]-4"-trans-(4-chlorophenyl)(trans-1,1':4',1"-tercyclohexane)
4'-trans-[(E)-2-chlorovinyl]-4"-trans-(4-bromophenyl)(trans-1,1':4',1"-tercyclohexane)
2-{4-trans-[(E)-2-chlorovinyl][1,1'-bicyclohexyl]-4-trans-yl}-1-[4-trans-(4-trifluoromethylphenyl)cyclohexyl]ethane
5-{2-[4'-trans-[(E)-2-chlorovinyl][1,1'-bicyclohexyl]-4-trans-yl]ethyl}-2-[4-(difluoromethoxy)phenyl]pyridine
2-{4-[4-trans-[(E)-2-chlorovinyl]cyclohexyl]phenyl}-5-(4-trans-pentylcyclohexyl)pyrimidine
4'-{4-trans-[5-trans-[(E)-2-chlorovinyl]-m-dioxane-2-yl]cyclohexyl}-4-biphenylcarbonitrile
4-{5-[2-[4'-trans-[(E)-2-chlorovinyl][1,1'-bicyclohexyl]-4-trans-yl]ethyl]-5-pyrimidinyl}-2-fluorobenzonitrile
3-(4'-chloro-3'-fluoro-4-biphenylyloxy)-1-{4'-trans-[(E)-2-chlorovinyl][1,1'-bicyclohexyl]-4-trans-yl}-(E)-1-propene
4trans-4-[(E)-2-chlorovinyl[-trans-4"'-[(3,4-difluorobenzyl)oxy][trans-1,1':4',1"-tercyclohexyl], m.p. (C-S) 86.4° C., S-N 112.8° C. cl.p. (N-I) 269.4° C.
trans-4-[(E)-2-chlorovinyl]-trans-4"-[(4-chloro-3-fluorobenzyl)oxy][trans-1,1':4',1"-tercyclohexyl]
trans-4-[(E)-2-chlorovinyl]-trans-4"-[(4-bromo-3-fluorobenzyl)oxy][trans-1,1':4',1"-tercyclohexyl]
4-trans-{[3-chloro-4-(trifluoromethyl)phenoxy]methyl}-1-{5-[-trans-[(E)-2-chlorovinyl]cyclohexyl]-m-dioxane-2-yl}cyclohexane
4'-{4-[4-trans-[(E)-2-chlorovinyl]cyclohexyl]phenyl}-1-[4-(difluoromethoxy)-3-methyl-4-biphenylyl]butane
4-trans-[(E)-2-chlorovinyl]-4"-trans-[(3,4-difluorophenyl)methoxy](trans-1,1':4',1"-tercyclohexane)
4-trans-[(E)-2-chlorovinyl]-4"-trans-[(4-chloro-3-fluorophenyl)methoxy]-(trans-1,1':4',1"-tercyclohexane)
4-trans-[(E)-2-chlorovinyl]-4"-trans-[(4-bromo-3-fluorophenyl)methoxy]-(trans-1,1':4',1"-tercyclohexane)
4'-trans-{4-[4-trans-[(E)-2-chlorovinyl]cyclohexyl]phenyl}-4-trans-(5,5,5-trifluoro-1-pentynyl)(1,1'-bicyclohexyl)
4-trans-[(E)-2-chlorovinyl]cyclohexyl 4-trans-[4'-(pentafluoroethoxy)-4-biphenylyl]carboxylate
4-(4-trans-propylcyclohexyl)phenylcarboxylic acid 4-{4-trans-[(E)-2-chlorovinyl]cyclohexyl}phenyl ester
4-{2-[4'-trans-[(E)-2-chlorovinyl][1,1'-bicyclohexyl]-4-trans-yl]ethyl}-1-(pentafluorophenyl)benzene
{4-trans-[(E)-2-chlorovinyl][trans-1,1':4',1"-tercyclohexane]-4"-trans-yl}pentafluorobenzoate
1-fluoro-4-{4-trans-[2-(4-trans-[(E)-2-chlorovinyl]cyclohexyl)ethyl]cyclohexyl}benzene
1-chloro-4-{4-trans-[2-(4-trans-[(E)-2-chlorovinyl]cyclohexyl)ethyl]cyclohexyl}benzene
1-bromo-4-{4-trans-[2-(4-trans-[(E)-2-chlorovinyl]cyclohexyl)ethyl]cyclohexyl}benzene
1-trifluoromethyl-4-{4-trans-[2-(4-trans-[(E)-2-chlorovinyl]cyclohexyl)ethyl]cyclohexyl}benzene
1-trifluoromethoxy-4-{4-trans-[2-(4-trans-[(E)-2-chlorovinyl]cyclohexyl)ethyl]cyclohexyl}benzene
1-difluoromethoxy-4-{4-trans-[2-(4-trans-[(E)-2-chlorovinyl]cyclohexyl)ethyl]cyclohexyl}benzene
4-{4-trans-[2-(4-trans-[(E)-2-chlorovinyl]cyclohexyl)ethyl]cyclohexyl}benzonitrile
4-{4-trans-[2-(4-trans-[(E)-2-chlorovinyl]cyclohexyl)ethyl]cyclohexyl}toluene
1-ethyl-4-{4-trans-[2-(4-trans-[(E)-2-chlorovinyl]cyclohexyl)ethyl]cyclohexyl}benzene
1-propyl-4-{4-trans-[2-(4-trans-[(E)-2-chlorovinyl]cyclohexyl)ethyl]cyclohexyl}benzene
1-methoxy-4-{4-trans-[2-(4-trans-[(E)-2-chlorovinyl]cyclohexyl)ethyl]cyclohexyl}benzene
1-ethoxy-4-{4-trans-[2-(4-trans-[(E)-2-chlorovinyl]cyclohexyl)ethyl]cyclohexyl}benzene
1-propyloxy-4-{4-trans-[2-(4-trans-[(E)-2-chlorovinyl]cyclohexyl)ethyl]cyclohexyl}benzene
1-methoxymethyl-4-{4-trans-[2-(4-trans-[(E)-2-chlorovinyl]cyclohexyl)ethyl]cyclohexyl}benzene.
2-trans-{4-trans-[(E)-2-chlorovinyl]cyclohexyl}-5-p-toluyl-m-dioxane, m.p. (C-N) 132.9° C., cl.p. (N-I) 187.5° C.;
2-trans-{4-trans-[(E)-2-chlorovinyl]cyclohexyl}-5-p-ethylphenyl-m-dioxane
2-trans-{4-trans-[(E)-2-chlorovinyl]cyclohexyl}-5-p-propylphenyl-m-dioxane
2-trans-{4-trans-[(E)-2-chlorovinyl]cyclohexyl}-5-p-butylphenyl-m-dioxane
2-trans-{4-trans-[(E)-2-chlorovinyl]cyclohexyl}-5-p-pentylphenyl-m-dioxane
2-trans-{4-trans-[(E)-2-chlorovinyl]cyclohexyl}-5-p-methoxyphenyl-m-dioxane
2-trans-{4-trans-[(E)-2-chlorovinyl]cyclohexyl}-5-p-ethoxyphenyl-m-dioxane
2-trans-{4-trans-[(E)-2-chlorovinyl]cyclohexyl}-5-p-propyloxyphenyl-m-dioxane
2-trans-{4-trans-[(E)-2-chlorovinyl]cyclohexyl}-5-p-methoxymethylphenyl-m-dioxane
2-{4-trans-[(E)-2-chlorovinyl]cyclohexyl}-5-p-toluyl-pyrimidine;
2-{4-trans-[(E)-2-chlorovinyl]cyclohexyl}-5-p-ethylphenyl-pyrimidine;
2-{4-trans-[(E)-2-chlorovinyl]cyclohexyl}-5-p-propylphenyl-pyrimidine;
2-{4-trans-[(E)-2-chlorovinyl]cyclohexyl}-5-p-butylphenyl-pyrimidine;
2-{4-trans-[(E)-2-chlorovinyl]cyclohexyl}-5-p-pentylphenyl-pyrimidine;

2-{4-trans-[(E)-2-chlorovinyl]cyclohexyl}-5-p-methoxyphenyl-pyrimidine;
2-{4-trans-[(E)-2-chlorovinyl]cyclohexyl}-5-p-ethoxyphenyl-pyrimidine;
2-{4-trans-[(E)-2-chlorovinyl]cyclohexyl}-5-p-propyloxyphenyl-pyrimidine;
2-{4-trans-[(E)-2-chlorovinyl]cyclohexyl}-5-p-methoxymethylphenyl-pyrimidine;
1-{4-trans-[(E)-2-chlorovinyl]cyclohexyl}-4-(5-methylpyrimidine)benzene;
1-{4-trans-[(E)-2-chlorovinyl]cyclohexyl}-4-(5-ethylpyrimidine)benzene;
1-{4-trans-[(E)-2-chlorovinyl]cyclohexyl}-4-(5-propylpyrimidine)benzene;
1-{4-trans-[(E)-2-chlorovinyl]cyclohexyl}-4-(5-butylpyrimidine)benzene;
1-{4-trans-[(E)-2-chlorovinyl]cyclohexyl}-4-(5-pentylpyrimidine)benzene;
1-{4-trans-[(E)-2-chlorovinyl]cyclohexyl}-4-(5-methoxypyrimidine)benzene;
1-{4-trans-[(E)-2-chlorovinyl]cyclohexyl}-4-(5-ethoxypyrimidine)benzene;
1-{4-trans-[(E)-2-chlorovinyl]cyclohexyl}-4-(5-propyloxypyrimidine)benzene;
1-{4-trans-[(E)-2-chlorovinyl]cyclohexyl}-4-(5-methoxymethylpyrimidine)benzene;
2-{4-trans-[(E)-2-chlorovinyl]cyclohexyl}-5-(4-trans-ethylcyclohexyl)pyrimidine;
2-{4-trans-[(E)-2-chlorovinyl]cyclohexyl}-5-(4-trans-propylcyclohexyl)pyrimidine;
2-{4-trans-[(E)-2-chlorovinyl]cyclohexyl}-5-(4-trans-butylcyclohexyl)pyrimidine, m.p. (S-N) 150.7° C., cl.p. (N-I) 211.2° C.;
2-{4-trans-[(E)-2-chlorovinyl]cyclohexyl}-5-(4-trans-pentylcyclohexyl)pyrimidine;
2-{4-trans-[(E)-2-chlorovinyl]cyclohexyl}-5-(4-trans-methoxycyclohexyl)pyrimidine;
2-{4-trans-[(E)-2-chlorovinyl]cyclohexyl}-5-(4-trans-ethoxycyclohexyl)pyrimidine;
2-{4-trans-[(E)-2-chlorovinyl]cyclohexyl}-5-(4-trans-propyloxycyclohexyl)pyrimidine;
2-{4-trans-[(E)-2-chlorovinyl]cyclohexyl}-5-(4-trans-methoxymethylcyclohexyl)pyrimidine;
2-{4-trans-[(E)-2-chlorovinyl]cyclohexyl}-5-(4-trans-vinylcyclohexyl)pyrimidine;
2-{4-trans-[(E)-2-chlorovinyl]cyclohexyl}-5-(4-trans-(1E-propenyl)cyclohexyl)pyrimidine;
2-{4-trans-[(E)-2-chlorovinyl]cyclohexyl}-5-(4-trans-(3-butenyl)cyclohexyl)pyrimidine;
2-{4-trans-[(E)-2-chlorovinyl]cyclohexyl}-5-(4-trans-(3E-pentenyl)cyclohexyl)pyrimidine;
2-{4-trans-[(E)-2-chlorovinyl]cyclohexyl}-5-(4-trans-(4-pentenyl)cyclohexyl)pyrimidine;
2-trans-{4'-trans-[(E)-2-chlorovinyl][1,1'-bicyclohexyl]-4-trans-yl}-5-ethyl-m-dioxane;
2-trans-{4'-trans-[(E)-2-chlorovinyl][1,1'-bicyclohexyl]-4-trans-yl}-5-propyl-m-dioxane;
2-trans-{4'-trans-[(E)-2-chlorovinyl][1,1'-bicyclohexyl]-4-trans-yl}-5-butyl-m-dioxane;
2-trans-{4'-trans-[(E)-2-chlorovinyl][1,1'-bicyclohexyl]-4-trans-yl}-5-pentyl-m-dioxane;
2-trans-{4'-trans-[(E)-2-chlorovinyl][1,1'-bicyclohexyl]-4-trans-yl}-5-methoxy-m-dioxane;
2-trans-{4'-trans-[(E)-2-chlorovinyl][1,1'-bicyclohexyl]-4-trans-yl}-5-ethoxy-m-dioxane;
2-trans-{4'-trans-[(E)-2-chlorovinyl][1,1'-bicyclohexyl]-4-trans-yl}-5-propyloxy-m-dioxane;
2-trans-{4'-trans-[(E)-2-chlorovinyl][1,1'-bicyclohexyl]-4-trans-yl}-5-methoxymethyl-m-dioxane;
2-trans-{4'-trans-[(E)-2-chlorovinyl][1,1'-bicyclohexyl]-4-trans-yl}-5-vinyl-m-dioxane;
2-trans-{4'-trans-[(E)-2-chlorovinyl][1,1'-bicyclohexyl]-4-trans-yl}-5-(1E-propenyl)-m-dioxane;
2-trans-{4'-trans-[(E)-2-chlorovinyl][1,1'-bicyclohexyl]-4-trans-yl}-5-(3-butenyl)-m-dioxane;
2-trans-{4'-trans-[(E)-2-chlorovinyl][1,1'-bicyclohexyl]-4-trans-yl}-5-(3E-pentenyl)-m-dioxane;
2-trans-{4'-trans-[(E)-2-chlorovinyl][1,1'-bicyclohexyl]-4-trans-yl}-5-(4-pentenyl)-m-dioxane;
1-{4-trans-[(E)-2-chlorovinyl]cyclohexyl}-4-{[5-trans-ethyl][2-yl]-m-dioxane}benzene;
1-{4-trans-[(E)-2-chlorovinyl]cyclohexyl}-4-{[5-trans-propyl][2-yl]-m-dioxane}benzene;
1-trans-{4'-trans-[(E)-2-chlorovinyl]cyclohexyl}-4-{[5-trans-butyl][2-yl]-m-dioxane}benzene;
1-{4-trans-[(E)-2-chlorovinyl]cyclohexyl}-4-{[5-trans-pentyl][2-yl]-m-dioxane}benzene;
1-{4-trans-[(E)-2-chlorovinyl]cyclohexyl}-4-{[5-trans-methoxy][2-yl]-m-dioxane}benzene;
1-{4-trans-[(E)-2-chlorovinyl]cyclohexyl}-4-{[5-trans-ethoxy][2-yl]-m-dioxane}benzene;
1-{4-trans-[(E)-2-chlorovinyl]cyclohexyl}-4-{[5-trans-propyloxy][2-yl]-m-dioxane}benzene;
1-{4-trans-[(E)-2-chlorovinyl]cyclohexyl}-4-{[5-trans-methoxymethyl][2-yl]-m-dioxane}benzene;
1-{4-trans-[(E)-2-chlorovinyl]cyclohexyl}-4-{[5-trans-vinyl][2-yl]-m-dioxane}benzene;
1-{4-trans-[(E)-2-chlorovinyl]cyclohexyl}-4-{[5-trans-(1E-propenyl)][2-yl]-m-dioxane}benzene;
1-{4-trans-[(E)-2-chlorovinyl]cyclohexyl}-4-{[5-trans-(3-butenyl)][2-yl]-m-dioxane}benzene;
1-{4-trans-[(E)-2-chlorovinyl]cyclohexyl}-4-{[5-trans-(3E-pentenyl)][2-yl]-m-dioxane}benzene;
1-{4-trans-[(E)-2-chlorovinyl]cyclohexyl}-4-{[5-trans-(4-pentenyl)][2-yl]-m-dioxane}benzene;

EXAMPLE 2

2.25 g of bromomethyltriphosphonium bromide were suspended in 10 ml of abs. tetrahydrofuran in a sulphonation flask while gassing with nitrogen and the suspension was cooled to −20° C. and treated with 0.61 g of potassium tert.-butylate. After stirring at −20° C. for 20 minutes a solution of 1 g of 4-[4'-trans-(1,1'-bicyclohexylcarboxaldehyde)-4-trans-yl]toluene in 10 ml of abs. tetrahydrofuran was added dropwise. The suspension was stirred at −20° C. for a further 40 minutes, thereafter poured into 80 ml of ice-cooled hexane and the colourless suspension was stirred at 0° C. for 30 minutes. The suspension was suction filtered and the filtrate was evaporated. The residue (2.02 g) was purified by chromatography on silica gel with hexane and subsequently recrystallized from hexane to give 0.1 g of 4-{4'-trans-[(E)-2-bromovinyl][1,1'-bicyclohexyl]-4-trans-yl}toluene, m.p. S-N 122.4° C., cl.p. (N-I) 231.9° C.

The following compounds can be manufactured in an analogous manner:

1-fluoro-4-{4'-trans-[(E)-2-bromovinyl][1,1'-bicyclohexyl]-4-trans-yl}-benzene
1-chloro-4-{4'-trans-[(E)-2-bromovinyl][1,1'-bicyclohexyl]-4-trans-yl}-benzene
1-bromo-4-{4'-trans-[(E)-2-bromovinyl][1,1'-bicyclohexyl]-4-trans-yl}benzene, m.p. (C-N) 207.0° C., cl.p. (N-I) 267.8° C.
1-cyano-4-{4'-trans-[(E)-2-bromovinyl][1,1'-bicyclohexyl]-4-trans-yl}-benzene 1-trifluoromethyl-4-{4'-trans-[(E)-2-bromovinyl][1,1'-bicyclohexyl]-4-trans-yl}-benzene
1-trifluoromethoxy-4-{4'-trans-[(E)-2-bromovinyl][1,1'-bicyclohexyl]-4-trans-yl}-benzene
1-difluoromethoxy-4-{4'-trans-[(E)-2-bromovinyl][1,1'-bicyclohexyl]-4-trans-yl}-benzene
1-ethyl-4-{4'-trans-[(E)-2-bromovinyl][1,1'-bicyclohexyl]-4-trans-yl}-benzene
1-propyl-4-{4'-trans-[(E)-2-bromovinyl][1,1'-bicyclohexyl]-4-trans-yl}-benzene
1-butyl-4-{4'-trans-[(E)-2-bromovinyl][1,1'-bicyclohexyl]-4-trans-yl}-benzene
1-pentyl-4-{4'-trans-[(E)-2-bromovinyl][1,1'-bicyclohexyl]-4-trans-yl}-benzene
1-methoxy-4-{4'-trans-[(E)-2-bromovinyl][1,1'-bicyclohexyl]-4-trans-yl}-benzene
1-ethoxy-4-{4'-trans-[(E)-2-bromovinyl][1,1'-bicyclohexyl]-4-trans-yl}-benzene
1-propyloxy-4-{4'-trans-[(E)-2-bromovinyl][1,1'-bicyclohexyl]-4-trans-yl}-benzene
1-methoxymethyl-4-{4'-trans-[(E)-2-bromovinyl][1,1'-bicyclohexyl]-4-trans-yl}-benzene
1-{4-trans-[(E)-2-bromovinyl]cyclohexyl}-4-ethylbenzene
4-trans-[(E)-2-bromovinyl]-4'-trans-cyclohexyl(1,1'-bicyclohexyl)
2-{4-trans-[(E)-2-bromovinyl]cyclohexyl}-5-[(E)-3pentenyl]pyridine
4-{2-[4-trans-[(E)-2-bromovinyl]cyclohexyl]ethyl}-3-fluoro-1-butylbenzene
2-{4-trans-[(E)-2-bromovinyl]cyclohexyl}-1-[4-(5,5,5-trifluoropentyl)phenyl]ethyne
4-trans-{2-[4-trans-[(E) -2-bromovinyl]cyclohexyl]ethyl}-1-(3,4,5-trifluorophenyl)cyclohexane
4'-{2-[4-trans-[(E)-2-bromovinyl]cyclohexyl]ethyl}-4-biphenylcarbonitrile
3-{4'-trans-[(E)-2-bromovinyl][1,1'-bicyclohexyl]-4-trans-yl}-1-{4-[(E)-4-pentenyl]phenoxy}propane
4-{2-[4-trans-[(E)-2-bromovinyl]cyclohexyl]ethyl}-2,3',3"-trifluoro-4"'-methyl-p-terphenyl
5-{4-[4-trans-[(E)-2-bromovinyl]cyclohexyl]-(E)-3-butenyl}-2-(2,3,5,6-tetrafluoro-4-trifluoromethoxy-4'-biphenylyl)-pyridine
4-{4'-trans-[(E)-2-bromovinyl][1,1'-bicyclohexyl][4-trans-yl]}phenylcarboxylic acid 4-cyano-3-fluorophenyl ester.
1,2-difluoro-4-{4'-trans-[{(E)-2-bromovinyl][1,1'-bicyclohexyl]-4-trans-yl}-benzene
1-chloro-4-{4'-trans-[{(E)-2-bromovinyl][1,1'-bicyclohexyl]-4-trans-yl}-2-fluorobenzene
1-bromo-4-{4'-trans-[{(E)-2-bromovinyl][1,1'-bicyclohexyl]-4-trans-yl}-2-fluorobenzene
1-cyano-4-{4'-trans-[{(E)-2-bromovinyl][1,1'-bicyclohexyl]-4-trans-yl}-2-fluorobenzene
1-trifluoromethyl-4-{4'-trans-[{(E)-2-bromovinyl][1,1'-bicyclohexyl]-4-trans-yl}-2-fluorobenzene
1-trifluoromethoxy-4-{4'-trans-[{(E)-2-bromovinyl][1,1'-bicyclohexyl]-4-trans-yl}-2-fluorobenzene
1-difluoromethoxy-4-{4'-trans-[{(E)-2-bromovinyl][1,1'-bicyclohexyl]-4-trans-yl}-2-fluorobenzene
1-methyl-4-{4'-trans-[{(E)-2-bromovinyl][1,1'-bicyclohexyl]-4-trans-yl}-2-fluorobenzene
1-ethyl-4-{4'-trans-[{(E)-2-bromovinyl][1,1'-bicyclohexyl]-4-trans-yl}-2-fluorobenzene
1-propyl-4-{4'-trans-[{(E)-2-bromovinyl][1,1'-bicyclohexyl]-4-trans-yl}-2-fluorobenzene
1-butyl-4-{4'-trans-[{(E)-2-bromovinyl][1,1'-bicyclohexyl]-4-trans-yl}-2-fluorobenzene
1-pentyl-4-{4'-trans-[{(E)-2-bromovinyl][1,1'-bicyclohexyl]-4-trans-yl}-2-fluorobenzene
1-methoxy-4-{4'-trans-[{(E)-2-bromovinyl][1,1'-bicyclohexyl]-4-trans-yl}-2-fluorobenzene
1-ethoxy-4-{4'-trans-[{(E)-2-bromovinyl][1,1'-bicyclohexyl]-4-trans-yl}-2-fluorobenzene
1-propyloxy-4-{4'-trans-[{(E)-2-bromovinyl][1,1'-bicyclohexyl]-4-trans-yl}-2-fluorobenzene
1-methoxymethyl-4-{4'-trans-[{(E)-2-bromovinyl][1,1'-bicyclohexyl]-4-trans-yl}-2-fluorobenzene
4-trans-[(E)-2-bromovinyl]-4'-trans-(4-fluorophenethyl)(1,1'-bicyclohexyl)
4-trans-[(E)-2-bromovinyl]-4'-trans-(4-chlorophenethyl)(1,1'-bicyclohexyl)
4-trans-[(E)-2-bromovinyl]-4'-trans-(4-bromophenethyl)(1,1'-bicyclohexyl)
4-trans-[(E)-2-bromovinyl]-4'-trans-(4-cyanophenethyl)(1,1'-bicyclohexyl)
4-trans-[(E)-2-bromovinyl]-4'-trans-(4-trifluoromethylphenethyl)(1,1'-bicyclohexyl)
4-trans-[(E)-2-bromovinyl]-4'-trans-(4-trifluoromethoxyphenethyl)(1,1'-bicyclohexyl)
4-trans-[(E)-2-bromovinyl]-4'-trans-(4-difluoromethoxyphenethyl)(1,1'-bicyclohexyl)
4-trans-[(E)-2-bromovinyl]-4'-trans-(4-methylphenethyl)(1,1'-bicyclohexyl)
4-trans-[(E)-2-bromovinyl]-4'-trans-(4-ethylphenethyl)(1,1'-bicyclohexyl)
4-trans-[(E)-2-bromovinyl]-4'-trans-(4-propylphenethyl)(1,1'-bicyclohexyl)
4-trans-[(E)-2-bromovinyl]-4'-trans-(4-butylphenethyl)(1,1'-bicyclohexyl)
4-trans-[(E)-2-bromovinyl]-4'-trans-(4-pentylphenethyl)(1,1'-bicyclohexyl)
4-trans-[(E)-2-bromovinyl]-4'-trans-(4-methoxyphenethyl)(1,1'-bicyclohexyl)
4-trans-[(E)-2-bromovinyl]-4'-trans-(4-ethoxyphenethyl)(1,1'-bicyclohexyl)
4-trans-[(E)-2-bromovinyl]-4'-trans-(4-propyloxyphenethyl)(1,1'-bicyclohexyl)
4-trans-[(E)-2-bromovinyl]-4'-trans-(4-(methoxymethyl)phenethyl)(1,1'-bicyclohexyl)
4-trans-[(E)-2-bromovinyl]-4'-trans-(3,4-difluorophenethyl)(1,1'-bicyclohexyl)
4-trans-[(E)-2-bromovinyl]-4'-trans-(3-fluoro-4-chlorophenethyl)(1,1'-bicyclohexyl)
4-trans-[(E)-2-bromovinyl]-4'-trans-(3-fluoro-4-bromophenethyl)(1,1'-bicyclohexyl)
4-trans-[(E)-2-bromovinyl]-4'-trans-(3-fluoro-4-cyanophenethyl)(1,1'-bicyclohexyl)
4-trans-[(E)-2-bromovinyl]-4'-trans-(3-fluoro-4-trifluoromethylphenethyl)(1,1'-bicyclohexyl)
4-trans-[(E)-2-bromovinyl]-4'-trans-(3-fluoro-4-trifluoromethoxyphenethyl)(1,1'-bicyclohexyl)
4-trans-[(E)-2-bromovinyl]-4'-trans-(3-fluoro-4-difluoromethoxyphenethyl)(1,1'-bicyclohexyl)
4-trans-[(E)-2-bromovinyl]-4'-trans-(3-fluoro-4-methylphenethyl)(1,1'-bicyclohexyl)
4-trans-[(E)-2-bromovinyl]-4'-trans-(3-fluoro-4-ethylphenethyl)(1,1'-bicyclohexyl)
4-trans-[(E)-2-bromovinyl]-4'-trans-(3-fluoro-4-propylphenethyl)(1,1'-bicyclohexyl)
4-trans-[(E)-2-bromovinyl]-4'-trans-(3-fluoro-4-butylphenethyl)(1,1'-bicyclohexyl)
4-trans-[(E)-2-bromovinyl]-4'-trans-(3-fluoro-4-pentylphenethyl)(1,1'-bicyclohexyl)

4-trans-[(E)-2-bromovinyl]-4'-trans-(3-fluoro-4-methoxyphenethyl)(1,1'-bicyclohexyl)

4-trans-[(E)-2-bromovinyl]-4'-trans-(3-fluoro-4-ethoxyphenethyl)(1,1'-bicyclohexyl)

4-trans-[(E)-2-bromovinyl]-4'-trans-(3-fluoro-4-propyloxyphenethyl)(1,1'-bicyclohexyl)

4-trans-[(E)-2-bromovinyl]-4'-trans-(3-fluoro-4-(methoxymethyl)phenethyl)(1,1'-bicyclohexyl)

EXAMPLE 3

1.40 g of chloromethyl-triphenylphosphonium chloride were suspended in 10 ml of abs. tetrahydrofuran in a sulphonation flask while gassing with nitrogen, cooled to $-20°$ C. and treated with 0.48 g of potassium tert.-butylate. After stirring at $-20°$ C. for 30 minutes a solution of 1 g of 4-trans-(4-chlorophenethyl)-4'-trans-(1,1'-bicyclohexylpropionaldehye) in 10 ml of abs. tetrahydrofuran was added dropwise to the yellow suspension. The suspension was stirred at $-20°$ C. for 40 minutes, poured into 60 ml of ice-cooled hexane, stirred at 0° C. for 30 minutes, and filtered; there were isolated from the filtrate 1.368 g of product which was purified firstly by chromatography on silica gel with hexane and then by crystallization from methylene chloride/methanol: 0.23 g of 4'-trans-[(E)-4-chloro-3-butenyl]-4-trans-(4-chlorophenethyl)(1,1'-bicylohexyl), m.p. (C-N) 98.1° C., cl.p. (N-I) 185.4° C.

The following compounds can be manufactured in an analogous manner:

4-{4-trans-[(E)-4-chloro-3-butenyl]cyclohexyl}toluene

1-[(E)-4-chloro-3-butenyl]-2,3-difluoro-4-(4-trans-heptylcyclohexyl)benzene

4-[(E)-4-chloro-3-butenyl]-3,2'-difluoro-4'-octylbiphenyl

1-[4-trans-(1-butynyl)cyclohexyl]-4-[(E)-4-chloro-3butenyl]benzene 2-trans-{4-trans-[(E)-4-chloro-3-butenyl]cyclohexyl}-5-(4-pentenyl)-m-dioxane 4-{4-trans-[(E)-4-chloro-3-butenyl]cyclohexyl}-2,6-difluoro-1-pentylbenzene 2-chloro-4-{4-[(E)-4-chloro-3-butenyl]phenethyl}-1-heptylbenzene 4-[(E)-4-chloro-3-butenyl]-2,3-difluoro-1-(4-trans-octylcyclohexyl)benzene 4-{4'-trans-[(E)-4-chloro-3-butenyl][1,1'-bicyclohexyl]-4-trans-yl}-1-fluorobenzene, m.p. (C-N) 82.9° C., cl.p. (N-I) 183.0° C.

4-{4'-trans-[(E)-4-chloro-3-butenyl][1,1'-bicyclohexyl]-4-trans-yl}-1-chlorobenzene 4-{4'-trans-[(E)-4-chloro-3-butenyl][1,1'-bicyclohexyl]-4-trans-yl}-1-bromobenzene 4-{4'-trans-[(E)-4-chloro-3-butenyl][1,1'-bicyclohexyl]-4 -trans-yl}-1-methylbenzene, m.p. (C-S) 69.2° C., S-N 76.0° C., cl.p. (N-I) 210.8° C.

2-{4-[(E)-4-chloro-3-butenyl]phenyl}-5-[2-(4-trans-hexylcyclohexyl)ethyl]pyrimidine 4-{2-[4'-trans-[(E)-4-chloro-3-butenyl][1,1'-bicyclohexyl]-4-trans-yl]ethyl}-2,6-difluorobenzonitrile 4-[(E)-4-chloro-3-butenyl]-3,2'-difluoro-4'-[4-trans -(3-heptynyl)cyclohexyl]biphenyl 2-trans-{4-trans-[(E)-4-chloro-3-butenyl]cyclohexyl}-5-{4-trans-[(E)-2-butenyloxy]cyclohexyl}-m-dioxane 1-trans-{4-[(E)-4-chloro-3-butenyl]phenyl}-4-[4-(3,4-dichlorophenyl)butyl]cyclohexane 4-chloro-4'-{4'-trans-[(E)-4-chloro-3-butenyl][1,1'-bicyclohexyl]-4-trans-yl}biphenyl 4-bromo-4'-{4'-trans-[(E)-4-chloro-3-butenyl][1,1'-bicyclohexyl]-4-trans-yl}biphenyl 4'-trans-{[4-[(E)-4-chloro-3-butenyl]phenoxy]methyl}-4-trans-[4-(trifluoromethoxy)phenyl](1,1'-bicyclohexyl)

4-{4-trans-[(E)-3-chloro-2-propenyloxy]cyclohexyl}toluene

1-[(E)-3-chloro-2-propenyloxy]-2,3-difluoro-4-(4-trans-heptylcyclohexyl) benzene 4-[(E)-3-chloro-2-propenyloxy]-3,2'-difluoro-4'-octylbiphenyl 1-[4-trans-(1-butynyl)cyclohexyl]-4-[(E)-3-chloro-2-propenyloxy]benzene 2-trans-{4-trans-[(E)-3-chloro-2-propenyloxy]cyclohexyl}-5-(4-pentenyl) -m-dioxane 4-{4-trans-[(E)-3-chloro-2-propenyloxy]cyclohexyl}-2,6-difluoro-1-pentylbenzene 2-chloro-4-{4-[(E)-3-chloro-2-propenyloxy]phenethyl}-1-heptylbenzene 4-[(E)-3-chloro-2-propenyloxy]-2,3-difluoro-1-(4-trans-octylcyclohexyl)benzene 4-{4'-trans-[(E)-3-chloro-2-propenyloxy][1,1'-bicyclohexyl]-4-trans-yl}-1-fluorobenzene, m.p. (C-N) 83.7° C., cl.p. (N-I) 142.3° C.

4-{4'-trans-[(E)-3-chloro-2-propenyloxy][1,1'-bicyclohexyl]-4-trans-yl}-1-chlorobenzene 4-{4'-trans-[(E)-3-chloro-2-propenyloxy][1,1'-bicyclohexyl]-4-trans-yl}-1-bromobenzene 4-{4'-trans-[(E)-3-chloro-2-propenyloxy][1,1'-bicyclohexyl]-4-trans-yl}-1-methylbenzene 2-{4-[(E)-3-chloro-2-propenyloxy]phenyl}-5-[2-(4-trans-hexylcyclohexyl)ethyl]pyrimidine 4-{2-[4'-trans-[(E)-3-chloro-2-propenyloxy][1,1'-bicyclohexyl]-4-trans-yl]ethyl}-2,6-difluorobenzonitrile 4-[(E)-3-chloro-2-propenyloxy]-3,2'-difluoro-4'-[4-trans-(3-heptynyl)cyclohexyl]biphenyl 2-trans-{4-trans-[(E)-3-chloro-2-propenyloxy]cyclohexyl}-5-{4-trans-[(E)-2-butenyloxy]cyclohexyl}-m-dioxane 1-trans-{4-[(E)-3-chloro-2-propenyloxy]phenyl}-4-[4-(3,4-dichlorophenyl)butyl]cyclohexane 4-chloro-4'-{4'-trans-[(E)-3-chloro-2-propenyloxy][1,1'-bicyclohexyl]-4-trans-yl}biphenyl 4-bromo-4'-{4'-trans-[(E)-3-chloro-2-propenyloxy][1,1'-bicyclohexyl]-4-trans-yl}biphenyl 4'-trans-{[4-[(E)-3-chloro-2-propenyloxy]phenoxy]methyl}-4-trans-[4-(trifluoromethoxy)phenyl](1,1'-bicyclohexyl).

EXAMPLE 4

Binary mixtures (BM) with 4-(trans-4-pentylcyclohexyl)benzonitrile were prepared in order to investigate the properties of the compounds of formula I in mixtures. The threshold potential and the response times were measured at 22° C. in a TN cell (low bias tilt) having a plate separation of 8 mm; the 2.5-fold value of the threshold potential ($V_{10}$) was chosen as the operating voltage. The corresponding data for 4-(trans-4-pentylcyclohexyl)benzonitrile are: cl.p. (N-I) 54.6° C., $V_{10}=1.62$ V, $t_{on}=22$ ms, $t_{off}=42$ ms, $\Delta n=0.120$.

BM-1

90 wt. % of 4-(trans-4-pentylcyclohexyl)benzonitrile 10 wt. % of 1-chloro-4-{2-[4-trans-((E)-2-chlorovinyl)cyclohexyl]ethyl}benzene cl.p. (N-I)=50.8° C., $V_{10}=1.56$ V, $t_{on}=24$ ms, $t_{off}=42$ ms, $\Delta n=0.122$;

BM-2

80 wt. % of 4-(trans-4-pentylcyclohexyl)benzonitrile 20 wt. % of 1-chloro-4-{2-[4-trans-((E)-2-chlorvinyl)cyclohexyl]ethyl}benzene cl.p. (N-I)=46.5° C., $V_{10}$=1.61 V, $t_{on}$=28 ms, $t_{off}$=43 ms, $\Delta n$=0.122;

BM-3
90 wt. % of 4-(trans-4-pentylcyclohexyl)benzonitrile
10 wt. % of 1-chloro-2-fluoro-4-{4-trans-[(E)-2-chlorvinyl]cyclohexyl}benzene
cl.p. (N-I)=47.7° C., $V_{10}$=1.56 V, $t_{on}$=38 ms, $t_{off}$=48 ms, $\Delta n$=0.120;

BM-4
80 wt. % of 4-(trans-4-pentylcyclohexyl)benzonitrile
20 wt. % of 1-chloro-2-fluoro-4-{4-trans-[(E)-2-chlorvinyl]cyclohexyl}benzene
cl.p. (N-I)=399° C., $\Delta n$=0.116;

BM-5
90 wt. % of 4-(trans-4-pentylcyclohexyl)benzonitrile
10 wt. % of 4'-trans-(4-chloro-3-fluorophenethyl)-4-trans-[(E)-2-chlorvinyl](1,1'-bicyclohexyl)
cl.p. (N-I)=62.2° C., $V_{10}$=1.65 V, $t_{on}$=31 ms, $t_{off}$=50 ms, $\Delta n$=0.126.

BM-6
80 wt. % of 4-(trans-4-pentylcyclohexyl)benzonitrile
20 wt. % of 4'-trans-(4-chloro-3-fluorophenethyl)-4-trans-[(E)-2-chlorvinyl](1,1'-bicyclohexyl)
cl.p. (N-I)=71.2° C., $V_{10}$=1.83 V, $t_{on}$=32 ms, $t_{off}$=49 ms, $\Delta n$=0.129.

BM-7
90 wt. % of 4-(trans-4-pentylcyclohexyl)benzonitrile
10 wt. % of 1,2-difluoro-4-{4'-trans-[(E)-2-chlorvinyl][1,1'-bicyclohexyl]-4-trans-yl}benzene
cl.p. (N-I)=60.7° C., $V_{10}$=1.54 V, $t_{on}$=28 ms, $t_{off}$=47 ms, $\Delta n$=0.120.

BM-8
80 wt. % of 4-(trans-4-pentylcyclohexyl)benzonitrile
20 wt. % of 1,2-difluoro-4-{4'-trans-[(E)-2-chlorvinyl][1,1'-bicyclohexyl]-4-trans-yl}benzene
cl.p. (N-I)=66.7° C., $V_{10}$=1.62 V, $t_{on}$=33 ms, $t_{off}$=50 ms, $\Delta n$=0.123.

BM-9
90 wt. % of 4-(trans-4-pentylcyclohexyl)benzonitrile
10 wt. % of 2-fluoro-4-{4'-trans-[(E)-2-chlorvinyl][1,1'-bicyclohexyl]-4-trans-yl}toluene
cl.p. (N-I)=63.2° C., $V_{10}$=1.68 V, $t_{on}$=26 ms, $t_{off}$=45 ms, $\Delta n$=0.124.

BM-10
80 wt. % of 4-(trans-4-pentylcyclohexyl)benzonitrile
20 wt. % of 2-fluoro-4-{4'-trans-[(E)-2-chlorvinyl][1,1'-bicyclohexyl]-4-trans-yl}toluene
cl.p. (N-I)=72.3° C., $V_{10}$=1.7 V, $t_{on}$=27 ms, $t_{off}$=45 ms, $\Delta n$=0.127.

BM-11
90 wt. % of 4-(trans-4-pentylcyclohexyl)benzonitrile
10 wt. % of 4'-trans-[(E)-4-chloro-3-butenyl]-4-trans-(4-chlorophenethyl)(1,1'-bicyclohexyl)
cl.p. (N-I)=64.4° C., $V_{10}$=1.83 V, $t_{on}$=24 ms, $t_{off}$=40 ms, $\Delta n$=0.124.

BM-12
80 wt. % of 4-(trans-4-pentylcyclohexyl)benzonitrile
20 wt. % of 4'-trans-[(E)-4-chloro-3-butenyl]-4-trans-(4chlorophenethyl)(1,1'-bicyclohexyl)
cl.p. (N-I)=74.8° C, $V_{10}$=2.03 V, $t_{on}$=26 ms, $t_{off}$=41 ms, $\Delta n$=0.126.

BM-13
90 wt. % of 4-(trans-4-pentylcyclohexyl)benzonitrile
10 wt. % of 4-trans-[(E)-2-chlorovinyl]-4'-trans-(4-fluorophenethyl)(1,1'-bicyclohexyl)
cl.p. (N-I) =62.6° C, $V_{10}$=1.74V, $t_{on}$=25 ms, $t_{off}$=41 ms, $\Delta n$=0.121.

BM-14
80 wt. % of 4-(trans-4-pentylcyclohexyl)benzonitrile
20 wt. % of 4-trans-[(E)-2-chlorovinyl]-4'-trans-(4-fluorophenethyl)(1,1'-bicyclohexyl)
cl.p. (N-I)=71.1° C., $V_{10}$=1.73 V, $t_{on}$=28 ms, $t_{off}$=42 ms, $\Delta n$=0.121.

BM-15
90 wt. % of 4-(trans-4-pentylcyclohexyl)benzonitrile
10 wt. % of 4-chloro-3-fluoro-4'-{4-trans-[(E)-2-chlorovinyl]cyclohexyl}-1,1'-biphenyl
cl.p. (N-I)=61.1° C., $V_{10}$=1.64 V, $t_{on}$=31 ms, $t_{off}$=46 ms.

BM-16
80 wt. % of 4-(trans-4-pentylcyclohexyl)benzonitrile
20 wt. % of 4-chloro-3-fluoro-4'-{4-trans-[(E)-2-chlorvinyl]-cyclohexyl}-1,1'-biphenyl
cl.p. (N-I)=69.4° C., $V_{10}$=1.75 V, $t_{on}$=30 ms, $t_{off}$=53 ms.

BM-17
90 wt. % of 4-(trans-4-pentylcyclohexyl)benzonitrile
10 wt. % of 1-chloro-2-fluoro-4'-{4-trans-[(E)-2-chlorvinyl]-[1,1'-bicyclohexyl]-4-trans-yl}benzene
cl.p. (N-I)=62.9° C., $V_{10}$=1.70 V, $t_{on}$26 ms, $t_{off}$=43 ms, $\Delta n$=0.125.

BM-18
80 wt. % of 4-(trans-4-pentylcyclohexyl)benzonitrile
20 wt. % of 1-chloro-2-fluoro-4'-{4-trans-[(E)-2-chlorvinyl]-[1,1'-bicyclohexyl]-4-trans-yl}benzene
cl.p. (N-I)=72.4° C., $V_{10}$=1.70 V, $t_{on}$=31 ms, $t_{off}$=48 ms, $\Delta n$=0.131.

BM-19
90 wt. % of 4-(trans-4-pentylcyclohexyl)benzonitrile
10 wt. % of 4-{4'-trans-[(E)-2-bromovinyl][1,1'-bicyclohexyl]-4-trans-yl}toluene
cl.p. (N-I)=64.1° C., $V_{10}$=1.61 V, $t_{on}$=30 ms, $t_{off}$=46 ms, $\Delta n$=0,128.

BM-20
80 wt. % of 4-(trans-4-pentylcyclohexyl)benzonitrile
20 wt. % of 4-{4'-trans-[(E)-2-bromovinyl][1,1'-bicyclohexyl]-4-trans-yl}toluene
cl.p. (N-I)=73.2° C., $V_{10}$=1.79 V, $t_{on}$=31 ms, $t_{off}$=48 ms, $\Delta n$=0.130.

BM-21
90 wt. % of 4-(trans-4-pentylcyclohexyl)benzonitrile
10 wt. % of 1-{trans-[(E)-2-chlorovinyl]cyclohexyl}-4-(4-trans-propylcyclohexyl)benzene
cl.p. (N-I)=62.3° C., $V_{10}$=1.67 V, $t_{on}$=26 ms, $t_{off}$=43 ms, $\Delta n$=0.124.

BM-22
80 wt. % of 4-(trans-4-pentylcyclohexyl)benzonitrile
20 wt. % of 1-{trans-[(E)-2-chlorovinyl]cyclohexyl}-4-(4-trans-propylcyclohexyl)benzene
cl.p. (N-I)=72.2° C., $V_{10}$=1.77 V, $t_{on}$=31 ms, $t_{off}$=46 ms, $\Delta n$=0.124.

BM-23
90 wt. % of 4-(trans-4-pentylcyclohexyl)benzonitrile
10 wt. % of 1-chloro-4-{4'-trans-[(E)-2-chlorvinyl][1,1'-bicyclohexyl]-4-trans-yl}benzene
cl.p. (N-I)=57.1° C., $V_{10}$=1.62 V, $t_{on}$=30 ms, $t_{off}$=44 ms, $\Delta n$=0.125.

BM-24
80 wt. % of 4-(trans-4-pentylcyclohexyl)benzonitrile
20 wt. % of 1-chloro-4-{4'-trans-[(E)-2-chlorvinyl][1,1'-bicyclohexyl]-4-trans-yl}benzene
cl.p. (N-I)=58.8° C., $V_{10}$=1.68 V, $t_{on}$=29 ms, $t_{off}$=45 ms.

BM-25
90 wt. % of 4-(trans-4-pentylcyclohexyl)benzonitrile 10 wt. % of 4-{4'-trans-[(E)-2-chlorovinyl][1,1'-bicyclohexyl]-4-trans-yl}toluene
cl.p. (N-I)=65.8° C., $V_{10}$=1.79 V, $t_{on}$=22 ms, $t_{off}$=37 ms, $\Delta n$=0.124.

BM-26
80 wt. % of 4-(trans-4-pentylcyclohexyl)benzonitrile
20 wt. % of 4-{4'-trans-[(E)-2-chlorovinyl][1,1'-bicyclohexyl]-4-trans-yl}toluene
cl.p. (N-I)=77.8° C., $V_{10}$=1.81 V, $t_{on}$=27 ms, $t_{off}$=44 ms.

BM-27
90 wt. % of 4-(trans-4-pentylcyclohexyl)benzonitrile
10 wt. % of 4-chloro-4'-{4-trans-[(E)-2-chlorvinyl]cyclohexyl}biphenyl
cl.p. (N-I)=65.7° C., $V_{10}$=1.77 V, $t_{on}$=25 ms, $t_{off}$=42 ms, $\Delta n$=0.123.

BM-28
80 wt. % of 4-(trans-4-pentylcyclohexyl)benzonitrile
20 wt. % of 4-chloro-4'-{4-trans-[(E)-2-chlorvinyl]cyclohexyl}biphenyl
cl.p. (N-I)=74.6° C., $V_{10}$=1.79 V, $t_{on}$=28 ms, $t_{off}$=41 ms, $\Delta n$=0.125.

BM-29
90 wt. % of 4-(trans-4-pentylcyclohexyl)benzonitrile
10 wt. % of 1-{4'-trans-[(E)-2-chlorovinyl][1,1'-bicyclohexyl]-4-trans-yl}-4-(4-trans-propylcyclohexyl)benzene
cl.p. (N-I)=63.4° C., $V_{10}$=1.74 V, $t_{on}$=25 ms, $t_{off}$=40 ms, $\Delta n$=1.24.

BM-30
80 wt. % of 4-(trans-4-pentylcyclohexyl)benzonitrile
20 wt. % of 1-{4'-trans-[(E)-2-chlorovinyl][1,1'-bicyclohexyl]-4-trans-yl}-4-(4-trans-propylcyclohexyl)benzene
cl.p. (N-I)=67.4° C., $V_{10}$=1.77 V, $t_{on}$=27 ms, $t_{off}$=44 ms, $\Delta n$=0.125.

BM-31
90 wt. % of 4-(trans-4-pentylcyclohexyl)benzonitrile
10 wt. % of 1-fluoro-4-{4'-trans-[(E)-2-chlorvinyl][1,1'-bicyclohexyl]-4-trans-yl}benzene
cl.p. (N-I)=63.2° C., $V_{10}$=1.73 V, $t_{on}$=24 ms, $t_{off}$=38 ms.

BM-32
80 wt. % of 4-(trans-4-pentylcyclohexyl)benzonitrile
20 wt. % of 1-fluoro-4-{4'-trans-[(E)-2-chlorvinyl][1,1'-bicyclohexyl]-4-trans-yl}benzene
cl.p. (N-I)=73.2° C., $V_{10}$=1.86 V, $t_{on}$=25 ms, $t_{off}$=40 ms.

BM-33
90 wt. % of 4-(trans-4-pentylcyclohexyl)benzonitrile
10 wt. % of 1-fluoro-4-{4'-trans-[(E)-4-chlor-3-butenyl][1,1'-bicyclohexyl]-4-trans-yl}benzene
cl.p. (N-I)=62.5° C., $V_{10}$=1.78 V, $t_{on}$=24 ms, $t_{off}$=40 ms, $\Delta n$=0.122.

BM-34
80 wt. % of 4-(trans-4-pentylcyclohexyl)benzonitrile
20 wt. % of 1-fluoro-4-{4'-trans-[(E)-4-chloro-3-butenyl][1,1'-bicyclohexyl]-4-trans-yl}benzene
cl.p. (N-I)=72.1° C., $V_{10}$=1.94 V, $t_{on}$=24 ms, $t_{off}$=40 ms.

BM-35
90 wt. % of 4-(trans-4-pentylcyclohexyl)benzonitrile
10 wt. % of 1-chloro-4-{4-trans-[(E)-2-chlorvinyl]cyclohexyl]benzene
cl.p. (N-I)=51° C., $V_{10}$=1.51 V, $t_{on}$=26 ms, $t_{off}$=43 ms, $\Delta n$=0.124.

BM-36
80 wt. % of 4-(trans-4-pentylcyclohexyl)benzonitrile
20 wt. % of 1-chloro-4-{4-trans-[(E)-2-chlorvinyl]cyclohexyl]benzene
cl.p. (N-I)=47° C., $V_{10}$=1.61 V, $t_{on}$=27 ms, $t_{off}$=43 ms, $\Delta n$=0.125.

BM-37
90 wt. % of 4-(trans-4-pentylcyclohexyl)benzonitrile
10 wt. % of 4-{4'-trans-[(E)-2-chlorovinyl][1,1'-bicyclohexyl]-4-trans-yl}benzonitrile
cl.p. (N-I)=70.4° C., $V_{10}$=1.83 V, $t_{on}$=26 ms, $t_{off}$=41 ms, $\Delta n$=0.133.

BM-38
80 wt. % of 4-(trans-4-pentylcyclohexyl)benzonitrile
20 wt. % of 4-{4'-trans-[(E)-2-chlorovinyl][1,1'-bicyclohexyl]-4-trans-yl}benzonitrile
cl.p. (N-I)=86.6° C., $V_{10}$=1.94 V, $t_{on}$=36 ms, $t_{off}$=51 ms, $\Delta n$=0.140.

BM-39
90 wt. % of 4-(trans-4-pentylcyclohexyl)benzonitrile
10 wt. % of 4-{4'-trans-[(E)-2-chlorovinyl][1,1'-bicyclohexyl]-4-trans-yl}-1-methoxybenzene
cl.p. (N-I)=67.8° C., $V_{10}$=1.77 V, $t_{on}$=24 ms, $t_{off}$=40 ms, $\Delta n$=0.128.

BM-40
80 wt. % of 4-(trans-4-pentylcyclohexyl)benzonitrile
20 wt. % of 4-{4'-trans-[(E)-2-chlorovinyl][1,1'-bicyclohexyl]-4-trans-yl}-1-methoxybenzene
cl.p. (N-I)=82.5° C., $V_{10}$=1.92 V, $t_{on}$=27 ms, $t_{off}$=43 ms, $\Delta n$=0.132.

BM-41
90 wt. % of 4-(trans-4-pentylcyclohexyl)benzonitrile
10 wt. % of 4-{4'-trans-[(E)-2-chlorovinyl][1,1'-bicyclohexyl]-4-trans-yl}-1-(trifluoromethoxy)benzene
cl.p. (N-I)=60.7° C., $V_{10}$=1.53 V, $t_{on}$=29 ms, $t_{off}$=47 ms, $\Delta n$=0.124.

BM-42
80 wt. % of 4-(trans-4-pentylcyclohexyl)benzonitrile
20 wt. % of 4-{4'-trans-[(E)-2-chlorovinyl][1,1'-bicyclohexyl]-4-trans-yl}-1-(trifluoromethoxy)benzene
cl.p. (N-I)=67.7° C., $V_{10}$=1.67 V, $t_{on}$=31 ms, $t_{off}$=47 ms, $\Delta n$=0.124.

BM-43
90 wt. % of 4-(trans-4-pentylcyclohexyl)benzonitrile
10 wt. % of 4-{4-trans-[(E)-2-chlorovinyl]cyclohexyl}-1-(trifluoromethoxy)benzene
cl.p. (N-I)=46.9° C., $V_{10}$=1.43 V, $t_{on}$=28 ms, $t_{off}$=46 ms, $\Delta n$=0.118.

BM-44
80 wt. % of 4-(trans-4-pentylcyclohexyl)benzonitrile
20 wt. % of 4-{4-trans-[(E)-2-chlorovinyl]cyclohexyl}-1-(trifluoromethoxy)benzene
cl.p. (N-I)=37.4° C., $V_{10}$=1.25 V, $t_{on}$=33 ms, $t_{off}$=53 ms, $\Delta n$=0.109.

BM-45
90 wt % of 4-(trans-4-pentylcyclohexyl)benzonitrile
10 wt % of 1-bromo-4-{4'-trans-[(E)-2-chlorovinyl][1,1'-bicyclohexyl]-4-trans-yl}benzene
cl.p. (N-I) 65.4° C., $V_{10}$=1.81 V, $t_{on}$=27 ms, $t_{off}$=43 ms. $\Delta n$=0.127.

BM-46
80 wt % of 4-(trans-4-pentylcyclohexyl)benzonitrile
20 wt % of 1-bromo-4-{4'-trans-[(E)-2-chlorovinyl][1,1'-bicyclohexyl]-4-trans-yl}benzene
cl.p. (N-I) 77.4° C., $\Delta n$=0.130.

BM-47
90 wt % of 4-(trans-4-pentylcyclohexyl)benzonitrile
10 wt % of 4'-trans-(4-bromophenethyl)-4-trans-[(E)-2-chlorovinyl](1,1'-bicyclohexyl)

cl.p. (N-I) 63.2° C., $V_{10}=1.80$ V, $t_{on}=25$ ms, $t_{off}=39$ ms, $\Delta n=0.124$.

BM-48

80 wt % of 4-(trans-4-pentylcyclohexyl)benzonitrile
20 wt % of 4'-trans-(4-bromophenethyl)-4-trans-[(E)-2-chlorovinyl](1,1'- bicyclohexyl)

cl.p. (N-I) 72.1° C., $V_{10}=1.81$ V, $t_{on}=31$ ms, $t_{off}$45 ms, $\Delta n=0.125$.

BM-49

90 wt % of 4-(trans-4-pentylcyclohexyl)benzonitrile
10 wt % of 1-bromo-4-{4'-trans-[(E)-2-bromovinyl][1.1'-bicyclohexyl]-4-trans-yl}benzene cl.p. (N-I) 62.8° C., $V_{10}=1.59$ V, $t_{on}=29$ ms, $t_{off}=46$ ms.

BM-50

80 wt % of 4-(trans-4-pentylcyclohexyl)benzonitrile
20 wt % of 1-bromo-4-{4'-trans-[(E)-2-bromovinyl][1,1'-bicyclohexyl]-4-trans-yl}benzene cl.p. (N-I) 73.3° C.

BM-51

90 wt % 4-(trans-4-pentylcyclohexyl)benzonitrile
10 wt % 2-{4-trans-[(E)-2-chlorovinyl]cyclohexyl}-5-(4-trans-butylcyclohexyl)-pyrimidine cl.p. (N-I) 60.8° C., $V_{10}=1.52$ V, $t_{on}=29$ ms, $t_{off}=45$ ms, $\Delta n=0,122$

BM-52

80 wt % 4-(trans-4-pentylcyclohexyl)benzonitrile
20 wt % 2- {4-trans-[(E)-2-chlorovinyl]cyclohexyl}-5-(4-trans-butylcyclohexyl)-pyrimidine cl.p. (N-I) 70.9° %, $V_{10}=1.54$ V, $t_{on}=37$ ms, $t_{off}=58$ ms, $\Delta n=0,122$

BM-53

90 wt % 4-(trans-4-pentylcyclohexyl)benzonitrile
10 wt % 2-trans-{4-trans-[(E)-2-chlorovinyl]cyclohexyl}-5-p-tolyl-m-dioxane cl.p. (N-I) 59.5° %, $V_{10}=1.56$ V, $t_{on}=28$ ms, $t_{off}=45$ ms, $\Delta n=0,124$

BM-54

80 wt % 4-(trans-4-pentylcyclohexyl)benzonitrile
20 wt % 2-trans-{4-trans-[(E)-2-chlorovinyl]cyclohexyl}-5-p-tolyl-m-dioxane cl.p. (N-I) 65.5° C., $V_{10}=1.46$ V, $t_{on}=38$ ms, $t_{off}=57$ ms, $\Delta n=0,125$

BM-55

90 wt % 4-(trans-4-pentylcyclohexyl)benzonitrile
10 wt % 2-trans-{4-trans-[(E)-2-chlorovinyl]cyclohexyl}-5-propyl-m-dioxane cl.p. (N-I), 50.7° C., $V_{10}=1.45$ V, $t_{on}=26$ ms, $t_{off}=46$ ms, $\Delta n=0,116$

BM-56

80 wt % 4-(trans-4-pentylcyclohexyl)benzonitrile
20 wt % 2-trans- {4-trans-[(E)-2-chlorovinyl]cyclohexyl}-5-propyl-m-dioxane cl.p. (N-I), 48.0° C., $V_{10}=1.30$ V, $t_{on}=31$ ms, $t_{off}=52$ ms, $\Delta n=0,110$

BM-57

90 wt % 4-(trans-4-pentylcyclohexyl)benzonitrile
10 wt % 4'-trans-[(E)-2-chlorovinyl]-4-trans-propyl-(1,1'-bicyclohexyl)

cl.p. (N-I), 55.3° C., $V_{10}=1.57$ V, $t_{on}=23$ ms, $t_{off}=44$ ms, $\Delta n=0,118$

BM-58

80 wt % 4-(trans-4-pentylcyclohexyl)benzonitrile
20 wt % 4'-trans-[(E)-2-chlorovinyl]-4-trans-propyl-(1,1'-bicyclohexyl)

cl.p. (N-I), 57.7° C., $V_{10}=1.60$ V, $t_{on}=25$ ms, $t_{off}=44$ ms, $\Delta n=0,114$

BM-59

90 wt % 4-(trans-4-pentylcyclohexyl)benzonitrile
10 wt % 4'-trans-[(E)-2-chlorovinyl]-4-trans-(1E-propenyl)(1,1'-bicyclohexyl)

cl.p. (N-I) 58.9° C., $V_{10}=1.65$ V, $t_{on}=24$ ms, $t_{off}=40$ ms, $\Delta n=0.122$

BM-60

80 wt % 4-(trans-4-pentylcyclohexyl)benzonitrile
20 wt % 4-trans-[(E)-2-chlorovinyl]-4-trans-(1E-propenyl)(1,1'-bicyclohexyl)

cl.p. (N-I) 63.7° C., $V_{10}=1.63$ V, $t_{on}=24$ ms, $t_{off}$37 ms, $\Delta n=0,122$

BM-61

90 wt % 4-(trans-4-pentylcyclohexyl)benzonitrile
10 wt % 4'-trans-[(E)-2-chlorovinyl]-4-trans-methoxymethyl-(1,1'-bicyclohexyl)

cl.p. (N-I) 54.9° C., $V_{10}=1.45$ V, $t_{on}=42$ ms, $t_{off}=59$ ms, $\Delta n=0,118$

BM-62

80 wt % 4-(trans-4-pentylcyclohexyl)benzonitrile
20 wt % 4'-trans-[(E)-2-chlorovinyl]-4-trans-methoxymethyl-(1,1'-bicyclohexyl)

cl.p. (N-I) 54.7° C., $V_{10}=1.48$ V, $t_{on}=42$ ms, $t_{off}=62$ ms, $\Delta n=0,113$

We claim:

1. Compounds of the formula

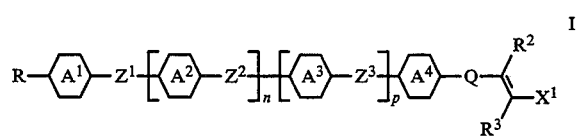

wherein
R signifies hydrogen, halogen, cyano, isothiocyanato, or alkyl, alkenyl or alkynyl with 1 to 15 carbon atoms, which is unsubstituted or substituted with at least one of halogen, cyano and/or trifluoromethyl and in which one or more non-adjacent —CH$_2$— groups can be replaced by —O—, —S—, —CO—, —COO— and/or —OOC—;

Q represents alkylene with 2 to 10 carbon atoms, which is unsubstituted or substituted with at least one fluorine and in which one —CH$_2$— group can be replaced by —O—, —S—, —COO— or —OOC—, or —CH$_2$—, —CF$_2$—, —CHF— or a single covalent bond;

A$^1$, A$^2$, A$^3$ each independently signify 1,4-phenylene, which is unsubstituted or substituted with at least one of halogen, cyano and/or methyl and in which, when it is unsubstituted, one or more —CH— groups can be replaced by nitrogen, or unsubstituted or cyano- or fluoro-substituted trans-1,4-cyclohexylene, or 1,4-cyclohexenylene, trans-1,3-dioxane-2,5-diyl or trans-1,3-dithiane-2,5-diyl;

A$^4$ represents unsubstituted or cyano- or fluoro-substituted trans-1,4-cyclohexylene, or 1,4-cyclohexenylene, trans-1,3-dioxane-2,5-diyl, trans-1,3-dithiane-2,5-diyl or, when Q is different from a single covalent bond, also 1,4-phenylene, which is unsubstituted or substituted with at least one of halogen, cyano and/or methyl and in which when it is unsubstituted, one or more —CH— groups can be replaced by nitrogen;

X$^1$ represents bromine or chlorine;
Z$^1$, Z$^2$, Z$^3$ each independently denote a single covalent bond, —CH$_2$—, —OCH$_2$—, —CH$_2$CH$_2$—, —COO—, —OOC—, —C≡C—, —(CH$_2$)$_4$—, —(CH$_2$)$_3$O—, —O(CH$_2$)$_3$—, the trans form of —CH=CH—, —CH=CHCH$_2$O—, —OCH$_2$CH=CH—, —CH=CH(CH$_2$)$_2$— or —(CH$_2$)$_2$CH=CH—;

n, p each independently signify 0 or 1;

R$^2$,R$^3$ each independently represent hydrogen or fluorine.

2. Compounds according to claim 1 of the formula

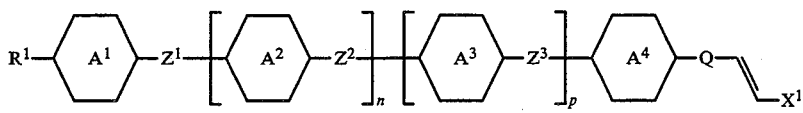

I-a wherein
- A$^1$,A$^2$,A$^3$ each independently represent 1,4-phenylene, which is unsubstituted or substituted with at least one of halogen and/or cyano, or pyridine-2,5-diyl pyrimidine-2,5-diyl, trans-1,4-cyclohexylene or trans-1,3-dioxane-2,5-diyl;
- A$^4$ represents trans-1,4-cyclohexylene, 1,3-dioxane-2,5-diyl or, when Q is different from a single covalent bond, also 1,4-phenylene, which is unsubstituted or substituted with at least one halogen, or pyridine-2,5-diyl or pyrimidine-2,5-diyl;
- Z$^1$,Z$^2$,Z$^3$ each independently represent a single covalent bond, —CH$_2$CH$_2$—, —CH$_2$O—, —OCH$_2$—, or —C≡C—;
- Q represents —CH$_2$CH$_2$—, —OCH$_2$— or a single covalent bond;
- R$^1$ represents hydrogen, alkyl, alkenyl or alkynyl with 1 to 7 carbon atoms, which is unsubstituted or substituted with at least one of halogen, cyano and/or trifluoromethyl and in which one —CH$_2$— group can be replaced by —O—, or, where ring A$^1$ represents an aromatic ring, also halogen or cyano;
- n,p each independently signify 0 or 1; and
- X$^1$ represents chlorine or bromine.

3. Compounds according to claim 1, wherein ring A$^4$ represents trans-1,4-cyclohexylene or, when Q is different from a single covalent bond, also 1,4-phenylene, which is unsubstituted or substituted with at least one halogen.

4. A liquid crystalline mixture containing at least two components, wherein at least one component is a compound of formula I defined in claim 1.

5. Compounds according to claim 2, wherein ring A$^4$ represents trans-1,4-cyclohexylene or, when Q is different from a single covalent bond, also 1,4-phenylene, which is unsubstituted or substituted with at least one halogen.

6. Compounds according to claim 1, wherein ring A$^4$ signifies trans-1,4-cyclohexylene, and Q signifies a single covalent bond.

7. Compounds according to claim 2, wherein ring A$^4$ signifies trans-1,4-cyclohexylene, and Q signifies a single covalent bond.

8. Compounds according to claim 3, wherein ring A$^4$ signifies trans-1,4-cycylohexylene, and Q signifies a single covalent bond.

9. Compounds according to claim 5, wherein ring A$^4$ signifies trans-1,4-cyclohexylene, and Q signifies a single covalent bond.

10. Compounds according to claim 1, wherein X$^1$ represents chlorine.

11. Compounds according to claim 2, wherein X$^1$ represents chlorine.

12. Compounds according to claim 3, wherein X$^1$ represents chlorine.

13. Compounds according to claim 5, wherein X$^1$ represents chlorine.

14. Compounds according to claim 6, wherein X$^1$ represents chlorine.

15. Compounds according to claim 7, wherein X$^1$ represents chlorine.

16. Compounds according to claim 8, wherein X$^1$ represents chlorine.

17. Compounds according to claim 9, wherein X$^1$ represents chlorine.

* * * * *

UNITED STATES PATENT AND TRADEMARK OFFICE
CERTIFICATE OF CORRECTION

PATENT NO. : 5,364,556
DATED : November 15, 1994
INVENTOR(S) : Martin Schadt and Frank Seils It is certified that error appears in the above-identified patent and that said Letters Patent is hereby corrected as shown below:

In claim 1, column 46, line 67, delete "$-CH_2-$" and insert therefor -- $-CH_2O-$ --.

In claim 8, column 48, line 25, delete "4-cycylohexylene," and insert therefor -- 4-cyclohexylene, --.

Signed and Sealed this

Twenty-first Day of February, 1995

Attest:

BRUCE LEHMAN

*Attesting Officer*   *Commissioner of Patents and Trademarks*